US012617869B2

(12) United States Patent　(10) Patent No.:　US 12,617,869 B2
Matsumoto et al.　(45) Date of Patent:　May 5, 2026

(54) ANTI-ADAMTS13 ANTIBODY AND USE THEREOF

(71) Applicants:Nara Medical University, Kashihara (JP); National Institutes of Biomedical Innovation, Health and Nutrition, Ibaraki City (JP); Alfresa Pharma Corporation, Osaka (JP)

(72) Inventors: Masanori Matsumoto, Kashihara (JP); Masaki Hayakawa, Kashihara (JP); Teruhito Yasui, Ibaraki City (JP); Takeharu Minamitani, Ibaraki City (JP)

(73) Assignees: Nara Medical University, Kashihara (JP); National Institutes of Biomedical Innovation, Health and Nutrition, Ibaraki City (JP); Alfresa Pharma Corporation, Osaka (JP)

( * ) Notice: Subject to any disclaimer, the term of this patent is extended or adjusted under 35 U.S.C. 154(b) by 493 days.

(21) Appl. No.: 18/548,856

(22) PCT Filed: Mar. 3, 2022

(86) PCT No.: PCT/JP2022/009106
§ 371 (c)(1),
(2) Date: Sep. 5, 2023

(87) PCT Pub. No.: WO2022/186331
PCT Pub. Date: Sep. 9, 2022

(65) Prior Publication Data
US 2024/0425614 A1　　Dec. 26, 2024

(30) Foreign Application Priority Data
Mar. 5, 2021　(JP) ................................. 2021-035392

(51) Int. Cl.
*C07K 16/40*　　(2006.01)
*G01N 33/573*　　(2006.01)

(52) U.S. Cl.
CPC ........... *C07K 16/40* (2013.01); *G01N 33/573* (2013.01); *C07K 2317/24* (2013.01); *C07K 2317/76* (2013.01); *C07K 2317/92* (2013.01); *G01N 2333/96486* (2013.01)

(58) Field of Classification Search
None
See application file for complete search history.

(56) References Cited

U.S. PATENT DOCUMENTS

2018/0362665 A1　12/2018　Vanhoorelbeke et al.
2020/0308303 A1　10/2020　Vanhoorelbeke et al.

FOREIGN PATENT DOCUMENTS

JP　　　2006-117537 A　　5/2006
WO　　WO 2017/097889 A1　6/2017
WO　　WO 2018/229103 A1　12/2018

OTHER PUBLICATIONS

Ito et al. Optimization of anti-ADAMTS13 antibodies for the treatment of ADAMTS13-related bleeding disorder in patients receiving circulatory assist device support. Scientific Reports | (Nov. 2021) 11:22341. (Year: 2021).*
Meyer et al. "Acquired von Willebrand Syndrome in Patients With a Centrifugal or Axial Continuous Flow Left Ventricular Assist Device." *JACC: Heart Failure* 2.2 (2014): 141-145.
Uemura et al. "Localization of ADAMTS13 to the stellate cells of human liver." *Blood* 106.3 (2005): 922-924.
Zander et al. "ADAMTS13 and von Willebrand factor interactions." *Current opinion in hematology* 22.5 (2015): 452-459.
International Search Report and Written Opinion issued in corresponding Patent Application No. PCT/JP2022/009106, dated May 24, 2022, in 6 pages.
International Preliminary Report on Patentability issued in corresponding Patent Application No. PCT/JP2022/009106, dated Aug. 29, 2023, in 6 pages.
Extended Search Report issued in corresponding European Patent Application No. 22763383.1, dated Mar. 18, 2025, in 10 pages.
Communication issued in corresponding European Patent Application No. 22763383.1, dated Jan. 13, 2026, in 3 pages.

* cited by examiner

*Primary Examiner* — Maher M Haddad
(74) *Attorney, Agent, or Firm* — Knobbe, Martens, Olson & Bear, LLP

(57)　　　ABSTRACT
A preparation of an antibody or an antibody derivative that can prevent or treat acquired von Willebrand syndrome (AVWS) accompanied by a disease in need of mechanical assisted circulation. The antibody or an antibody derivative has specific binding activity against ADAMTS13, von Willebrand factor (VWF) cleaving protease, which is a causative factor of the acquired von Willebrand syndrome (AVWS) in humans, and can reduce the excessive cleavage of VWF by ADAMTS13.

15 Claims, 4 Drawing Sheets

Specification includes a Sequence Listing.

Change in high molecular weight VMF multimer deficiency by shear stress and inhibition by A10 antibody

SEQUENCE LISTING

```
<160> NUMBER OF SEQ ID NOS: 64

<210> SEQ ID NO 1
<211> LENGTH: 8
<212> TYPE: PRT
<213> ORGANISM: Mus musculus

<400> SEQUENCE: 1

Gly Tyr Ser Phe Thr Gly Tyr Thr
1               5

<210> SEQ ID NO 2
<211> LENGTH: 8
<212> TYPE: PRT
<213> ORGANISM: Mus musculus

<400> SEQUENCE: 2

Ile Asn Pro Tyr Asn Gly Gly Thr
1               5

<210> SEQ ID NO 3
<211> LENGTH: 10
<212> TYPE: PRT
<213> ORGANISM: Mus musculus

<400> SEQUENCE: 3

Ala Arg Thr Ser Gly Tyr Leu Phe Ala Tyr
1               5                   10

<210> SEQ ID NO 4
<211> LENGTH: 6
```

-continued

```
<212> TYPE: PRT
<213> ORGANISM: Mus musculus

<400> SEQUENCE: 4

Glu Asp Ile Tyr Asn Arg
1               5

<210> SEQ ID NO 5

<400> SEQUENCE: 5

000

<210> SEQ ID NO 6
<211> LENGTH: 9
<212> TYPE: PRT
<213> ORGANISM: Mus musculus

<400> SEQUENCE: 6

Gln Gln Tyr Trp Ser Ser Pro Leu Thr
1               5

<210> SEQ ID NO 7
<211> LENGTH: 8
<212> TYPE: PRT
<213> ORGANISM: Mus musculus

<400> SEQUENCE: 7

Gly Phe Ser Leu Pro Arg Tyr Gly
1               5

<210> SEQ ID NO 8
<211> LENGTH: 7
<212> TYPE: PRT
<213> ORGANISM: Mus musculus

<400> SEQUENCE: 8

Ile Trp Ala Gly Gly Ser Thr
1               5

<210> SEQ ID NO 9
<211> LENGTH: 11
<212> TYPE: PRT
<213> ORGANISM: Mus musculus

<400> SEQUENCE: 9

Ala Arg Ala Gly Gly Ser Gln Pro Phe Asp Tyr
1               5                   10

<210> SEQ ID NO 10
<211> LENGTH: 6
<212> TYPE: PRT
<213> ORGANISM: Mus musculus

<400> SEQUENCE: 10

Arg Asp Ile Asn Thr Tyr
1               5

<210> SEQ ID NO 11

<400> SEQUENCE: 11

000

<210> SEQ ID NO 12
```

-continued

```
<211> LENGTH: 9
<212> TYPE: PRT
<213> ORGANISM: Mus musculus

<400> SEQUENCE: 12

Leu Gln Tyr Asp Glu Phe Pro Trp Thr
1               5

<210> SEQ ID NO 13
<211> LENGTH: 8
<212> TYPE: PRT
<213> ORGANISM: Mus musculus

<400> SEQUENCE: 13

Gly Phe Ser Leu Thr Arg Tyr Gly
1               5

<210> SEQ ID NO 14
<211> LENGTH: 7
<212> TYPE: PRT
<213> ORGANISM: Mus musculus

<400> SEQUENCE: 14

Ile Trp Ala Gly Gly Ser Thr
1               5

<210> SEQ ID NO 15
<211> LENGTH: 11
<212> TYPE: PRT
<213> ORGANISM: Mus musculus

<400> SEQUENCE: 15

Ala Arg Ala Gly Gly Ser Ser Ser Phe Asp Tyr
1               5                   10

<210> SEQ ID NO 16
<211> LENGTH: 6
<212> TYPE: PRT
<213> ORGANISM: Mus musculus

<400> SEQUENCE: 16

Gln Asp Ile Asn Thr Tyr
1               5

<210> SEQ ID NO 17

<400> SEQUENCE: 17

000

<210> SEQ ID NO 18
<211> LENGTH: 9
<212> TYPE: PRT
<213> ORGANISM: Mus musculus

<400> SEQUENCE: 18

Leu Gln Tyr Asp Glu Phe Pro Trp Thr
1               5

<210> SEQ ID NO 19
<211> LENGTH: 8
<212> TYPE: PRT
<213> ORGANISM: Mus musculus

<400> SEQUENCE: 19
```

```
Gly Phe Ser Leu Thr Gly Tyr Gly
1               5

<210> SEQ ID NO 20
<211> LENGTH: 7
<212> TYPE: PRT
<213> ORGANISM: Mus musculus

<400> SEQUENCE: 20

Ile Trp Ala Asp Gly Thr Thr
1               5

<210> SEQ ID NO 21
<211> LENGTH: 11
<212> TYPE: PRT
<213> ORGANISM: Mus musculus

<400> SEQUENCE: 21

Ala Arg Ala Gly Gly Ser Gln Pro Phe Asp Tyr
1               5                   10

<210> SEQ ID NO 22
<211> LENGTH: 6
<212> TYPE: PRT
<213> ORGANISM: Mus musculus

<400> SEQUENCE: 22

Gln Asp Ile Asn Ser Tyr
1               5

<210> SEQ ID NO 23

<400> SEQUENCE: 23

000

<210> SEQ ID NO 24
<211> LENGTH: 9
<212> TYPE: PRT
<213> ORGANISM: Mus musculus

<400> SEQUENCE: 24

Leu Gln Tyr Asp Glu Phe Pro Trp Thr
1               5

<210> SEQ ID NO 25
<211> LENGTH: 117
<212> TYPE: PRT
<213> ORGANISM: Mus musculus

<400> SEQUENCE: 25

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30

Thr Met His Trp Val Lys Gln Ser His Gly Lys Asn Leu Glu Trp Ile
        35                  40                  45

Gly Leu Ile Asn Pro Tyr Asn Gly Gly Thr Gly Tyr Asn Gln Lys Phe
    50                  55                  60

Lys Gly Lys Ala Thr Leu Thr Val Asp Lys Ser Ser Ser Thr Thr Tyr
65                  70                  75                  80

Ile Glu Leu Leu Ser Leu Thr Ser Glu Asp Ser Ala Val Tyr Tyr Cys
                85                  90                  95
```

```
Ala Arg Thr Ser Gly Tyr Leu Phe Ala Tyr Trp Gly Gln Gly Thr Leu
            100                 105                 110

Val Thr Val Ser Ala
        115

<210> SEQ ID NO 26
<211> LENGTH: 107
<212> TYPE: PRT
<213> ORGANISM: Mus musculus

<400> SEQUENCE: 26

Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Ile Phe Ser Ile Thr Ser Leu Gln Thr
65                  70                  75                  80

Glu Asp Val Ala Thr Tyr Tyr Cys Gln Gln Tyr Trp Ser Ser Pro Leu
                85                  90                  95

Thr Phe Gly Ala Gly Thr Lys Leu Glu Leu Lys
            100                 105

<210> SEQ ID NO 27
<211> LENGTH: 117
<212> TYPE: PRT
<213> ORGANISM: Unknown
<220> FEATURE:
<223> OTHER INFORMATION: Humanized

<400> SEQUENCE: 27

Gln Ile His Leu Val Glu Ser Gly Gly Gly Val Val Gln Thr Gly Lys
1               5                   10                  15

Ser Met Lys Ile Ser Cys Lys Ala Ser Gly Tyr Ser Phe Thr Gly Tyr
            20                  25                  30

Thr Met His Trp Val Lys Gln Thr Pro Gly Lys Asn Leu Glu Trp Ile
            35                  40                  45

Gly Leu Ile Asn Pro Tyr Asn Gly Gly Thr Gly Tyr Asn Gln Lys Phe
        50                  55                  60

Lys Gly Lys Ala Thr Leu Thr Val Asp Lys Ser Ser Ser Thr Thr Tyr
65                  70                  75                  80

Ile Glu Leu Leu Ser Leu Thr Ser Glu Asp Ser Ala Val Tyr Tyr Cys
                85                  90                  95

Ala Arg Thr Ser Gly Tyr Leu Phe Ala Tyr Trp Gly Gln Gly Thr Leu
            100                 105                 110

Val Thr Val Ser Ser
        115

<210> SEQ ID NO 28
<211> LENGTH: 107
<212> TYPE: PRT
<213> ORGANISM: Unknown
<220> FEATURE:
<223> OTHER INFORMATION: Humanized

<400> SEQUENCE: 28
```

```
Glu Thr Val Met Thr Gln Ser Pro Ala Thr Leu Ser Val Ser Pro Gly
1               5                   10                  15

Glu Arg Ala Thr Ile Thr Cys Lys Ala Ser Glu Asp Ile Tyr Asn Arg
            20                  25                  30

Leu Ala Trp Tyr Gln Gln Lys Pro Gly Gln Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Val Ala Thr Tyr Tyr Cys Gln Gln Tyr Trp Ser Ser Pro Leu
                85                  90                  95

Thr Phe Gly Ala Gly Thr Lys Leu Glu Ile Lys
            100                 105
```

<210> SEQ ID NO 29
<211> LENGTH: 117
<212> TYPE: PRT
<213> ORGANISM: Unknown
<220> FEATURE:
<223> OTHER INFORMATION: Humanized

<400> SEQUENCE: 29

```
Gln Val Gln Leu Val Gln Ser Gly Gly Gln Val Lys Lys Pro Gly Ala
1               5                   10                  15

Ser Val Lys Ile Ser Cys Lys Ala Ser Gly Tyr Ser Phe Thr Gly Tyr
            20                  25                  30

Thr Met His Trp Val Lys Gln Ala Pro Gly Arg Gly Leu Glu Trp Ile
        35                  40                  45

Gly Leu Ile Asn Pro Tyr Asn Gly Gly Thr Gly Tyr Asn Gln Lys Phe
    50                  55                  60

Lys Gly Lys Ala Thr Leu Thr Val Asp Lys Ser Ser Ser Thr Thr Tyr
65                  70                  75                  80

Ile Glu Leu Leu Ser Leu Thr Ser Glu Asp Ser Ala Val Tyr Tyr Cys
                85                  90                  95

Ala Arg Thr Ser Gly Tyr Leu Phe Ala Tyr Trp Gly Gln Gly Thr Leu
            100                 105                 110

Val Thr Val Ser Ser
        115
```

<210> SEQ ID NO 30
<211> LENGTH: 107
<212> TYPE: PRT
<213> ORGANISM: Unknown
<220> FEATURE:
<223> OTHER INFORMATION: Humanized

<400> SEQUENCE: 30

```
Asp Ile Val Leu Thr Gln Thr Pro Asp Ser Leu Ala Val Ser Leu Gly
1               5                   10                  15

Glu Arg Ala Thr Ile Thr Cys Lys Ala Ser Glu Asp Ile Tyr Asn Arg
            20                  25                  30

Leu Ala Trp Tyr Gln Gln Lys Ala Gly Gln Pro Pro Lys Leu Leu Ile
        35                  40                  45

Ser Gly Ala Thr Ser Leu Glu Thr Gly Val Pro Asp Arg Phe Ser Gly
    50                  55                  60

Ser Gly Ser Gly Thr Asp Phe Thr Leu Thr Ile Ser Ser Leu Gln Ala
```

```
65                70                75                80

Glu Asp Val Ala Thr Tyr Tyr Cys Gln Gln Tyr Trp Ser Ser Pro Leu
                85                90                95

Thr Phe Gly Ala Gly Thr Lys Val Asn Ile Lys
            100               105

<210> SEQ ID NO 31
<211> LENGTH: 117
<212> TYPE: PRT
<213> ORGANISM: Mus musculus

<400> SEQUENCE: 31

Gln Val Gln Leu Arg Glu Ser Gly Pro Gly Leu Val Ala Pro Ser Gln
1               5                 10                15

Ser Leu Ser Ile Thr Cys Thr Val Ser Gly Phe Ser Leu Pro Arg Tyr
                20                25                30

Gly Ile His Trp Val Arg Gln Pro Pro Gly Lys Gly Leu Glu Trp Leu
            35                40                45

Gly Val Ile Trp Ala Gly Gly Ser Thr Asp Tyr Asp Ser Ala Leu Met
        50                55                60

Ser Arg Leu Ser Ile Ser Lys Asp Thr Ser Lys Ser Gln Val Phe Leu
65                70                75                80

Lys Met Ser Ser Leu Gln Thr Asp Asp Thr Ala Ile Tyr Tyr Cys Ala
                85                90                95

Arg Ala Gly Gly Ser Gln Pro Phe Asp Tyr Trp Gly Gln Gly Thr Thr
            100               105               110

Leu Thr Val Ser Ser
        115

<210> SEQ ID NO 32
<211> LENGTH: 107
<212> TYPE: PRT
<213> ORGANISM: Mus musculus

<400> SEQUENCE: 32

Asp Ile Lys Met Thr Gln Ser Pro Ser Ser Met Tyr Ala Ser Leu Gly
1               5                 10                15

Glu Arg Val Thr Ile Thr Cys Lys Ala Ser Arg Asp Ile Asn Thr Tyr
                20                25                30

Leu Ser Trp Phe Gln Gln Lys Pro Gly Lys Ser Pro Lys Thr Leu Ile
            35                40                45

Ser Arg Ala Asn Arg Leu Val Asp Gly Val Pro Ser Arg Phe Ser Gly
        50                55                60

Ser Gly Ser Gly Gln Asp Tyr Ser Leu Ser Ile Ser Ser Leu Glu Tyr
65                70                75                80

Glu Asp Met Gly Phe Tyr Tyr Cys Leu Gln Tyr Asp Glu Phe Pro Trp
                85                90                95

Thr Phe Gly Gly Gly Thr Lys Leu Val Ile Lys
            100               105

<210> SEQ ID NO 33
<211> LENGTH: 117
<212> TYPE: PRT
<213> ORGANISM: Mus musculus

<400> SEQUENCE: 33

Gln Val Gln Leu Lys Glu Ser Gly Pro Gly Leu Val Ala Pro Ser Gln
1               5                 10                15
```

```
Ser Leu Ser Ile Thr Cys Thr Val Ser Gly Phe Ser Leu Thr Arg Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Lys Ser Ala Leu Met
    50                  55                  60

Ser Arg Leu Asn Ile Thr Lys Asp Asn Ser Lys Ser Gln Val Phe Leu
65                  70                  75                  80

Lys Met Asn Gly Leu Gln Thr Asp Asp Thr Ala Ile Tyr Phe Cys Ala
                85                  90                  95

Arg Ala Gly Gly Ser Ser Ser Phe Asp Tyr Trp Gly Gln Gly Thr Thr
            100                 105                 110

Leu Thr Val Ser Ser
        115

<210> SEQ ID NO 34
<211> LENGTH: 107
<212> TYPE: PRT
<213> ORGANISM: Mus musculus

<400> SEQUENCE: 34

Asp Ile Lys Met Thr Gln Ser Pro Ser Ser Met Asn Ala Ser Leu Gly
1               5                   10                  15

Glu Arg Val Thr Ile Thr Cys Lys Ala Ser Gln Asp Ile Asn Thr Tyr
            20                  25                  30

Leu Gly Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Gly Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Trp
                85                  90                  95

Thr Phe Gly Gly Gly Thr Lys Leu Glu Ile Lys
            100                 105

<210> SEQ ID NO 35
<211> LENGTH: 117
<212> TYPE: PRT
<213> ORGANISM: Mus musculus

<400> SEQUENCE: 35

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Ile His Trp Val Arg Gln Pro Pro Gly Lys Gly Leu Glu Trp Leu
        35                  40                  45

Gly Val Ile Trp Ala Asp Gly Thr Thr Asn Ser Asn Ser Ala Leu Met
    50                  55                  60

Ser Arg Leu Ser Ile Ser Lys Asp Asn Ser Lys Ser Gln Val Phe Leu
65                  70                  75                  80

Lys Met Thr Ser Leu Gln Thr Asp Asp Thr Ala Met Tyr His Cys Ala
                85                  90                  95

Arg Ala Gly Gly Ser Gln Pro Phe Asp Tyr Trp Gly Gln Gly Thr Thr
            100                 105                 110
```

```
Leu Thr Val Ser Ser
        115

<210> SEQ ID NO 36
<211> LENGTH: 107
<212> TYPE: PRT
<213> ORGANISM: Mus musculus

<400> SEQUENCE: 36

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Glu Ile Tyr Tyr Cys Leu Gln Tyr Asp Glu Phe Pro Trp
                85                  90                  95

Thr Phe Gly Gly Gly Thr Lys Leu Glu Ile Lys
            100                 105

<210> SEQ ID NO 37
<211> LENGTH: 488
<212> TYPE: PRT
<213> ORGANISM: Unknown
<220> FEATURE:
<223> OTHER INFORMATION: Humanized Chimera

<400> SEQUENCE: 37

Met Cys Pro Met Ser Ser Pro Gln Thr Leu Asn Thr Leu Thr Pro Thr
1               5                   10                  15

Met Gly Trp Ser Trp Ile Phe Leu Phe Leu Leu Ser Gly Thr Ala Gly
            20                  25                  30

Val Arg Ser Glu Val Gln Leu Gln Gln Ser Gly Pro Glu Leu Val Lys
        35                  40                  45

Pro Gly Thr Ser Met Lys Ile Ser Cys Lys Ala Ser Gly Tyr Ser Phe
    50                  55                  60

Thr Gly Tyr Thr Met His Trp Val Lys Gln Ser His Gly Lys Asn Leu
65                  70                  75                  80

Glu Trp Ile Gly Leu Ile Asn Pro Tyr Asn Gly Gly Thr Gly Tyr Asn
                85                  90                  95

Gln Lys Phe Lys Gly Lys Ala Thr Leu Thr Val Asp Lys Ser Ser Ser
            100                 105                 110

Thr Thr Tyr Ile Glu Leu Leu Ser Leu Thr Ser Glu Asp Ser Ala Val
            115                 120                 125

Tyr Tyr Cys Ala Arg Thr Ser Gly Tyr Leu Phe Ala Tyr Trp Gly Gln
        130                 135                 140

Gly Thr Leu Val Thr Val Ser Ala Ala Lys Thr Thr Pro Pro Ser Val
145                 150                 155                 160

Tyr Pro Leu Ala Pro Gly Cys Gly Asp Thr Thr Gly Ser Ser Val Thr
                165                 170                 175

Leu Gly Cys Leu Val Lys Gly Tyr Phe Pro Glu Ser Val Thr Val Thr
            180                 185                 190
```

-continued

```
Trp Asn Ser Gly Ser Leu Ser Ser Ser Val His Thr Phe Pro Ala Leu
        195                 200                 205

Leu Gln Ser Gly Leu Tyr Thr Met Ser Ser Ser Val Thr Val Pro Ser
        210                 215                 220

Ser Thr Trp Pro Ser Gln Thr Val Thr Cys Ser Val Ala His Pro Ala
225                 230                 235                 240

Ser Ser Thr Thr Val Asp Lys Lys Leu Glu Pro Ser Gly Pro Ile Ser
                245                 250                 255

Thr Ile Asn Pro Cys Pro Pro Cys Lys Glu Cys His Lys Cys Pro Ala
                260                 265                 270

Pro Asn Leu Glu Gly Gly Pro Ser Val Phe Ile Phe Pro Pro Asn Ile
        275                 280                 285

Lys Asp Val Leu Met Ile Ser Leu Thr Pro Lys Val Thr Cys Val Val
        290                 295                 300

Val Asp Val Ser Glu Asp Asp Pro Asp Val Gln Ile Ser Trp Phe Val
305                 310                 315                 320

Asn Asn Val Glu Val His Thr Ala Gln Thr Gln Thr His Arg Glu Asp
                325                 330                 335

Tyr Asn Ser Thr Ile Arg Val Val Ser Thr Leu Pro Ile Gln His Gln
                340                 345                 350

Asp Trp Met Ser Gly Lys Glu Phe Lys Cys Lys Val Asn Asn Lys Asp
        355                 360                 365

Leu Pro Ser Pro Ile Glu Arg Thr Ile Ser Lys Ile Lys Gly Leu Val
        370                 375                 380

Arg Ala Pro Gln Val Tyr Ile Leu Pro Pro Pro Ala Glu Gln Leu Ser
385                 390                 395                 400

Arg Lys Asp Val Ser Leu Thr Cys Leu Val Val Gly Phe Asn Pro Gly
                405                 410                 415

Asp Ile Ser Val Glu Trp Thr Ser Asn Gly His Thr Glu Glu Asn Tyr
                420                 425                 430

Lys Asp Thr Ala Pro Val Leu Asp Ser Asp Gly Ser Tyr Phe Ile Tyr
        435                 440                 445

Ser Lys Leu Asn Met Lys Thr Ser Lys Trp Glu Lys Thr Asp Ser Phe
        450                 455                 460

Ser Cys Asn Val Arg His Glu Gly Leu Lys Asn Tyr Tyr Leu Lys Lys
465                 470                 475                 480

Thr Ile Ser Arg Ser Pro Gly Lys
                485
```

```
<210> SEQ ID NO 38
<211> LENGTH: 241
<212> TYPE: PRT
<213> ORGANISM: Unknown
<220> FEATURE:
<223> OTHER INFORMATION: Humanized Chimera

<400> SEQUENCE: 38

Met Ser Gly His Ser Arg Asn Met Lys Phe Pro Ser Gln Leu Leu Leu
1                   5                   10                  15

Leu Leu Leu Phe Gly Ile Pro Gly Met Ile Cys Asp Ile Gln Met Thr
                20                  25                  30

Gln Ser Ser Ser Ser Phe Ser Val Ser Leu Gly Asp Arg Val Thr Ile
        35                  40                  45

Thr Cys Lys Ala Ser Glu Asp Ile Tyr Asn Arg Leu Ala Trp Tyr Gln
        50                  55                  60
```

```
Gln Lys Pro Gly Asn Ala Pro Arg Leu Leu Ile Ser Gly Ala Thr Ser
65                  70                  75                  80

Leu Glu Thr Gly Val Pro Ser Arg Phe Ser Gly Ser Gly Ser Gly Lys
                85                  90                  95

Asp Tyr Ile Phe Ser Ile Thr Ser Leu Gln Thr Glu Asp Val Ala Thr
                100                 105                 110

Tyr Tyr Cys Gln Gln Tyr Trp Ser Ser Pro Leu Thr Phe Gly Ala Gly
            115                 120                 125

Thr Lys Leu Glu Leu Lys Arg Ala Asp Ala Ala Pro Thr Val Ser Ile
        130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
                180                 185                 190

Gln Asp Ser Lys Asp Ser Thr Tyr Ser Met Ser Ser Thr Leu Thr Leu
            195                 200                 205

Thr Lys Asp Glu Tyr Glu Arg His Asn Ser Tyr Thr Cys Glu Ala Thr
        210                 215                 220

His Lys Thr Ser Thr Ser Pro Ile Leu Lys Ser Phe Asn Arg Asn Glu
225                 230                 235                 240

Cys
```

```
<210> SEQ ID NO 39
<211> LENGTH: 447
<212> TYPE: PRT
<213> ORGANISM: Unknown
<220> FEATURE:
<223> OTHER INFORMATION: Humanized

<400> SEQUENCE: 39
```

```
Gln Ile His Leu Val Glu Ser Gly Gly Gly Val Val Gln Thr Gly Lys
1               5                   10                  15

Ser Met Lys Ile Ser Cys Lys Ala Ser Gly Tyr Ser Phe Thr Gly Tyr
            20                  25                  30

Thr Met His Trp Val Lys Gln Thr Pro Gly Lys Asn Leu Glu Trp Ile
        35                  40                  45

Gly Leu Ile Asn Pro Tyr Asn Gly Gly Thr Gly Tyr Asn Gln Lys Phe
    50                  55                  60

Lys Gly Lys Ala Thr Leu Thr Val Asp Lys Ser Ser Ser Thr Thr Tyr
65                  70                  75                  80

Ile Glu Leu Leu Ser Leu Thr Ser Glu Asp Ser Ala Val Tyr Tyr Cys
                85                  90                  95

Ala Arg Thr Ser Gly Tyr Leu Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Arg Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

-continued

```
                 180              185              190
Leu Gly Thr Gln Thr Tyr Ile Cys Asn Val Asn His Lys Pro Ser Asn
             195              200              205

Thr Lys Val Asp Lys Lys Val Glu Pro Lys Ser Cys Asp Lys Thr His
             210              215              220

Thr Cys Pro Pro Cys Pro Ala Pro Glu Leu Leu Gly Gly Pro Ser Val
225              230              235              240

Phe Leu Phe Pro Pro Lys Pro Lys Asp Thr Leu Met Ile Ser Arg Thr
             245              250              255

Pro Glu Val Thr Cys Val Val Val Asp Val Ser His Glu Asp Pro Glu
             260              265              270

Val Lys Phe Asn Trp Tyr Val Asp Gly Val Glu Val His Asn Ala Lys
             275              280              285

Thr Lys Pro Arg Glu Glu Gln Tyr Asn Ser Thr Tyr Arg Val Val Ser
             290              295              300

Val Leu Thr Val Val His Gln Asp Trp Leu Asn Gly Lys Glu Tyr Lys
305              310              315              320

Cys Lys Val Ser Asn Lys Ala Leu Pro Ala Pro Ile Glu Lys Thr Ile
             325              330              335

Ser Lys Ala Lys Gly Gln Pro Arg Glu Pro Gln Val Tyr Thr Leu Pro
             340              345              350

Pro Ser Arg Asp Glu Leu Thr Lys Asn Gln Val Ser Leu Thr Cys Leu
             355              360              365

Val Lys Gly Phe Tyr Pro Ser Asp Ile Ala Val Glu Trp Glu Ser Asn
             370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
             405              410              415

Trp Gln Gln Gly Asn Val Phe Ser Cys Ser Val Met His Glu Ala Leu
             420              425              430

His Asn His Tyr Thr Gln Lys Ser Leu Ser Leu Ser Pro Gly Lys
             435              440              445
```

```
<210> SEQ ID NO 40
<211> LENGTH: 214
<212> TYPE: PRT
<213> ORGANISM: Unknown
<220> FEATURE:
<223> OTHER INFORMATION: Humanized

<400> SEQUENCE: 40

Glu Thr Val Met Thr Gln Ser Pro Ala Thr Leu Ser Val Ser Pro Gly
1               5                10               15

Glu Arg Ala Thr Ile Thr Cys Lys Ala Ser Glu Asp Ile Tyr Asn Arg
             20               25               30

Leu Ala Trp Tyr Gln Gln Lys Pro Gly Gln Ala Pro Arg Leu Leu Ile
         35               40               45

Ser Gly Ala Thr Ser Leu Glu Thr Gly Val Pro Ser Arg Phe Ser Gly
         50               55               60

Ser Gly Ser Gly Thr Glu Phe Thr Leu Thr Ile Ser Ser Leu Gln Ser
65               70               75               80

Glu Asp Val Ala Thr Tyr Tyr Cys Gln Gln Tyr Trp Ser Ser Pro Leu
             85               90               95

Thr Phe Gly Ala Gly Thr Lys Leu Glu Ile Lys Arg Thr Val Ala Ala
```

-continued

```
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 447
<212> TYPE: PRT
<213> ORGANISM: Unknown
<220> FEATURE:
<223> OTHER INFORMATION: Humanized

<400> SEQUENCE: 41

Gln Val Gln Leu Val Gln Ser Gly Gly Gln Val Lys Lys Pro Gly Ala
1                 5                 10                 15

Ser Val Lys Ile Ser Cys Lys Ala Ser Gly Tyr Ser Phe Thr Gly Tyr
                20                 25                 30

Thr Met His Trp Val Lys Gln Ala Pro Gly Arg Gly Leu Glu Trp Ile
            35                 40                 45

Gly Leu Ile Asn Pro Tyr Asn Gly Gly Thr Gly Tyr Asn Gln Lys Phe
        50                 55                 60

Lys Gly Lys Ala Thr Leu Thr Val Asp Lys Ser Ser Ser Thr Thr Tyr
65                 70                 75                 80

Ile Glu Leu Leu Ser Leu Thr Ser Glu Asp Ser Ala Val Tyr Tyr Cys
                85                 90                 95

Ala Arg Thr Ser Gly Tyr Leu Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                    245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Ile Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 42
<211> LENGTH: 214
<212> TYPE: PRT
<213> ORGANISM: Unknown
<220> FEATURE:
<223> OTHER INFORMATION: Humanized

<400> SEQUENCE: 42

Asp Ile Val Leu Thr Gln Thr Pro Asp Ser Leu Ala Val Ser Leu Gly
1               5                   10                  15

Glu Arg Ala Thr Ile Thr Cys Lys Ala Ser Glu Asp Ile Tyr Asn Arg
                20                  25                  30

Leu Ala Trp Tyr Gln Gln Lys Ala Gly Gln Pro Pro Lys Leu Leu Ile
            35                  40                  45

Ser Gly Ala Thr Ser Leu Glu Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Thr Tyr Tyr Cys Gln Gln Tyr Trp Ser Ser Pro Leu
                85                  90                  95

Thr Phe Gly Ala Gly Thr Lys Val Asn Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
                165             170             175
Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
        195             200             205

Phe Asn Arg Gly Glu Cys
        210

<210> SEQ ID NO 43
<211> LENGTH: 460
<212> TYPE: PRT
<213> ORGANISM: Mus musculus

<400> SEQUENCE: 43

Met Ala Val Leu Val Leu Phe Leu Cys Leu Val Ala Phe Pro Ser Cys
1               5               10              15

Val Leu Ser Gln Val Gln Leu Arg Glu Ser Gly Pro Gly Leu Val Ala
        20              25              30

Pro Ser Gln Ser Leu Ser Ile Thr Cys Thr Val Ser Gly Phe Ser Leu
        35              40              45

Pro Arg Tyr Gly Ile His Trp Val Arg Gln Pro Pro Gly Lys Gly Leu
        50              55              60

Glu Trp Leu Gly Val Ile Trp Ala Gly Gly Ser Thr Asp Tyr Asp Ser
65              70              75              80

Ala Leu Met Ser Arg Leu Ser Ile Ser Lys Asp Thr Ser Lys Ser Gln
                85              90              95

Val Phe Leu Lys Met Ser Ser Leu Gln Thr Asp Asp Thr Ala Ile Tyr
        100             105             110

Tyr Cys Ala Arg Ala Gly Gly Ser Gln Pro Phe Asp Tyr Trp Gly Gln
        115             120             125

Gly Thr Thr Leu Thr Val Ser Ser Ala Lys Thr Thr Pro Pro Ser Val
        130             135             140

Tyr Pro Leu Ala Pro Gly Ser Ala Ala Gln Thr Asn Ser Met Val Thr
145             150             155             160

Leu Gly Cys Leu Val Lys Gly Tyr Phe Pro Glu Pro Val Thr Val Thr
                165             170             175

Trp Asn Ser Gly Ser Leu Ser Ser Gly Val His Thr Phe Pro Ala Val
                180             185             190

Leu Gln Ser Asp Leu Tyr Thr Leu Ser Ser Ser Val Thr Val Pro Ser
        195             200             205

Ser Thr Trp Pro Ser Glu Thr Val Thr Cys Asn Val Ala His Pro Ala
        210             215             220

Ser Ser Thr Lys Val Asp Lys Lys Ile Val Pro Arg Asp Cys Gly Cys
225             230             235             240

Lys Pro Cys Ile Cys Thr Val Pro Glu Val Ser Ser Val Phe Ile Phe
                245             250             255

Pro Pro Lys Pro Lys Asp Val Leu Thr Ile Thr Leu Thr Pro Lys Val
        260             265             270

Thr Cys Val Val Val Asp Ile Ser Lys Asp Asp Pro Glu Val Gln Phe
        275             280             285

Ser Trp Phe Val Asp Asp Val Glu Val His Thr Ala Gln Thr Gln Pro
        290             295             300

Arg Glu Glu Gln Phe Asn Ser Thr Phe Arg Ser Val Ser Glu Leu Pro
305             310             315             320
```

-continued

```
Ile Met His Gln Asp Trp Leu Asn Gly Lys Glu Phe Lys Cys Arg Val
            325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
            355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
            435                 440                 445

His Thr Glu Lys Ser Leu Ser His Ser Pro Gly Lys
    450                 455                 460

<210> SEQ ID NO 44
<211> LENGTH: 236
<212> TYPE: PRT
<213> ORGANISM: Mus musculus

<400> SEQUENCE: 44

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
                20                  25                  30

Met Tyr Ala Ser Leu Gly Glu Arg Val Thr Ile Thr Cys Lys Ala Ser
            35                  40                  45

Arg Asp Ile Asn Thr Tyr Leu Ser Trp Phe Gln Gln Lys Pro Gly Lys
    50                  55                  60

Ser Pro Lys Thr Leu Ile Ser Arg Ala Asn Arg Leu Val Asp Gly Val
65                  70                  75                  80

Pro Ser Arg Phe Ser Gly Ser Gly Ser Gly Gln Asp Tyr Ser Leu Ser
                85                  90                  95

Ile Ser Ser Leu Glu Tyr Glu Asp Met Gly Phe Tyr Tyr Cys Leu Gln
            100                 105                 110

Tyr Asp Glu Phe Pro Trp Thr Phe Gly Gly Gly Thr Lys Leu Val Ile
            115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
            195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Trp
225                 230                 235
```

-continued

<210> SEQ ID NO 45
<211> LENGTH: 460
<212> TYPE: PRT
<213> ORGANISM: Mus musculus

<400> SEQUENCE: 45

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Arg Tyr Gly Val His Trp Val Arg Gln Pro Pro Gly Lys Gly Leu
    50                  55                  60

Glu Trp Leu Gly Val Ile Trp Ala Gly Gly Ser Thr Asn Tyr Lys Ser
65                  70                  75                  80

Ala Leu Met Ser Arg Leu Asn Ile Thr Lys Asp Asn Ser Lys Ser Gln
                85                  90                  95

Val Phe Leu Lys Met Asn Gly Leu Gln Thr Asp Asp Thr Ala Ile Tyr
            100                 105                 110

Phe Cys Ala Arg Ala Gly Gly Ser Ser Ser Phe Asp Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
            195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
            245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
            275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
            355                 360                 365

Glu Gln Met Ala Lys Asp Lys Val Ser Leu Thr Cys Met Ile Thr Asp

-continued

```
            370              375              380

Phe Phe Pro Glu Asp Ile Thr Val Glu Trp Gln Trp Asn Gly Gln Pro
385              390              395              400

Ala Glu Asn Tyr Lys Asn Thr Gln Pro Ile Met Asp Thr Asp Gly Ser
                405              410              415

Tyr Phe Val Tyr Ser Lys Leu Asn Val Gln Lys Ser Asn Trp Glu Ala
                420              425              430

Gly Asn Thr Phe Thr Cys Ser Val Leu His Glu Gly Leu His Asn His
            435              440              445

His Thr Glu Lys Ser Leu Ser His Ser Pro Gly Lys
        450              455              460

<210> SEQ ID NO 46
<211> LENGTH: 236
<212> TYPE: PRT
<213> ORGANISM: Mus musculus

<400> SEQUENCE: 46

Met Asp Met Arg Thr Pro Ala Gln Phe Leu Gly Ile Leu Leu Leu Trp
1               5               10              15

Phe Pro Gly Ile Lys Cys Asp Ile Lys Met Thr Gln Ser Pro Ser Ser
                20              25              30

Met Asn Ala Ser Leu Gly Glu Arg Val Thr Ile Thr Cys Lys Ala Ser
            35              40              45

Gln Asp Ile Asn Thr Tyr Leu Gly Trp Phe Gln Gln Lys Pro Gly Lys
        50              55              60

Ser Pro Lys Thr Leu Ile Tyr Arg Ala Asn Arg Leu Val Asp Gly Val
65              70              75              80

Pro Ser Arg Phe Ser Gly Ser Gly Ser Gly Gln Gly Tyr Ser Leu Thr
                85              90              95

Ile Ser Ser Leu Glu Tyr Glu Asp Met Gly Ile Tyr Tyr Cys Leu Gln
                100             105             110

Tyr Asp Glu Phe Pro Trp Thr Phe Gly Gly Gly Thr Lys Leu Glu Ile
            115             120             125

Lys Arg Ala Asp Ala Ala Pro Thr Val Ser Ile Phe Pro Pro Ser Ser
        130             135             140

Glu Gln Leu Thr Ser Gly Gly Ala Ser Val Val Cys Phe Leu Asn Asn
145             150             155             160

Phe Tyr Pro Lys Asp Ile Asn Val Lys Trp Lys Ile Asp Gly Ser Glu
                165             170             175

Arg Gln Asn Gly Val Leu Asn Ser Trp Thr Asp Gln Asp Ser Lys Asp
            180             185             190

Ser Thr Tyr Ser Met Ser Ser Thr Leu Thr Leu Thr Lys Asp Glu Tyr
            195             200             205

Glu Arg His Asn Ser Tyr Thr Cys Glu Ala Thr His Lys Thr Ser Thr
        210             215             220

Ser Pro Ile Val Lys Ser Phe Asn Arg Asn Glu Cys
225             230             235

<210> SEQ ID NO 47
<211> LENGTH: 472
<212> TYPE: PRT
<213> ORGANISM: Mus musculus

<400> SEQUENCE: 47

Met Ala Val Leu Val Leu Phe Leu Cys Leu Val Ala Phe Pro Ser Cys
```

-continued

```
1               5               10              15

Val Leu Ser Gln Val Gln Leu Lys Glu Ser Gly Pro Gly Leu Val Ala
            20              25              30

Pro Ser Gln Ser Leu Ser Ile Thr Cys Thr Val Ser Gly Phe Ser Leu
            35              40              45

Thr Gly Tyr Gly Ile His Trp Val Arg Gln Pro Pro Gly Lys Gly Leu
    50              55              60

Glu Trp Leu Gly Val Ile Trp Ala Asp Gly Thr Thr Asn Ser Asn Ser
65              70              75              80

Ala Leu Met Ser Arg Leu Ser Ile Ser Lys Asp Asn Ser Lys Ser Gln
                85              90              95

Val Phe Leu Lys Met Thr Ser Leu Gln Thr Asp Asp Thr Ala Met Tyr
            100             105             110

His Cys Ala Arg Ala Gly Gly Ser Gln Pro Phe Asp Tyr Trp Gly Gln
            115             120             125

Gly Thr Thr Leu Thr Val Ser Ser Ala Lys Thr Thr Pro Pro Ser Val
            130             135             140

Tyr Pro Leu Ala Pro Gly Cys Gly Asp Thr Thr Gly Ser Ser Val Thr
145             150             155             160

Leu Gly Cys Leu Val Lys Gly Tyr Phe Pro Glu Ser Val Thr Val Thr
            165             170             175

Trp Asn Ser Gly Ser Leu Ser Ser Ser Val His Thr Phe Pro Ala Leu
            180             185             190

Leu Gln Ser Gly Leu Tyr Thr Met Ser Ser Ser Val Thr Val Pro Ser
            195             200             205

Ser Thr Trp Pro Ser Gln Thr Val Thr Cys Ser Val Ala His Pro Ala
    210             215             220

Ser Ser Thr Thr Val Asp Lys Lys Leu Glu Pro Ser Gly Pro Ile Ser
225             230             235             240

Thr Ile Asn Pro Cys Pro Pro Cys Lys Glu Cys His Lys Cys Pro Ala
            245             250             255

Pro Asn Leu Glu Gly Gly Pro Ser Val Phe Ile Phe Pro Pro Asn Ile
            260             265             270

Lys Asp Val Leu Met Ile Ser Leu Thr Pro Lys Val Thr Cys Val Val
            275             280             285

Val Asp Val Ser Glu Asp Asp Pro Asp Val Gln Ile Ser Trp Phe Val
    290             295             300

Asn Asn Val Glu Val His Thr Ala Gln Thr Gln Thr His Arg Glu Asp
305             310             315             320

Tyr Asn Ser Thr Ile Arg Val Val Ser Thr Leu Pro Ile Gln His Gln
            325             330             335

Asp Trp Met Ser Gly Lys Glu Phe Lys Cys Lys Val Asn Asn Lys Asp
            340             345             350

Leu Pro Ser Pro Ile Glu Arg Thr Ile Ser Lys Ile Lys Gly Leu Val
            355             360             365

Arg Ala Pro Gln Val Tyr Ile Leu Pro Pro Pro Ala Glu Gln Leu Ser
            370             375             380

Arg Lys Asp Val Ser Leu Thr Cys Leu Val Val Gly Phe Asn Pro Gly
385             390             395             400

Asp Ile Ser Val Glu Trp Thr Ser Asn Gly His Thr Glu Glu Asn Tyr
            405             410             415

Lys Asp Thr Ala Pro Val Leu Asp Ser Asp Gly Ser Tyr Phe Ile Tyr
            420             425             430
```

-continued

```
Ser Lys Leu Asn Met Lys Thr Ser Lys Trp Glu Lys Thr Asp Ser Phe
        435                 440                 445

Ser Cys Asn Val Arg His Glu Gly Leu Lys Asn Tyr Tyr Leu Lys Lys
        450                 455                 460

Thr Ile Ser Arg Ser Pro Gly Lys
465                 470

<210> SEQ ID NO 48
<211> LENGTH: 234
<212> TYPE: PRT
<213> ORGANISM: Mus musculus

<400> SEQUENCE: 48

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
                20                  25                  30

Ala Ser Leu Gly Glu Arg Val Thr Ile Thr Cys Lys Ala Ser Gln Asp
        35                  40                  45

Ile Asn Ser Tyr Leu Ser Trp Phe Gln Gln Lys Pro Gly Lys Ser Pro
        50                  55                  60

Lys Thr Leu Ile Phe Arg Ala Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Glu Ile Tyr Tyr Cys Leu Gln Tyr Asp
            100                 105                 110

Glu Phe Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
        210                 215                 220

Ile Val Lys Ser Phe Asn Arg Asn Glu Trp
225                 230

<210> SEQ ID NO 49
<211> LENGTH: 23
<212> TYPE: DNA
<213> ORGANISM: Artificial Sequence
<220> FEATURE:
<223> OTHER INFORMATION: Forward primer for A10 ab

<400> SEQUENCE: 49
aagcagtggt atcaacgcag agt                                        23

<210> SEQ ID NO 50
<211> LENGTH: 30
<212> TYPE: DNA
```

-continued

<213> ORGANISM: Artificial Sequence
<220> FEATURE:
<223> OTHER INFORMATION: Reverse primer for A10 ab and 9A7 ab

<400> SEQUENCE: 50
taggacctga gagctttgtg ggtgctgagc                                    30

<210> SEQ ID NO 51
<211> LENGTH: 32
<212> TYPE: DNA
<213> ORGANISM: Artificial Sequence
<220> FEATURE:
<223> OTHER INFORMATION: Forward primer for A10 ab

<400> SEQUENCE: 51
ggggcggccg cagagtggcc attacggccg gg                                 32

<210> SEQ ID NO 52
<211> LENGTH: 35
<212> TYPE: DNA
<213> ORGANISM: Artificial Sequence
<220> FEATURE:
<223> OTHER INFORMATION: Reverse primer for A10 ab and 9A7 ab

<400> SEQUENCE: 52
ggggaattct catttacccg gagaccggga gatgg                              35

<210> SEQ ID NO 53
<211> LENGTH: 20
<212> TYPE: DNA
<213> ORGANISM: Artificial Sequence
<220> FEATURE:
<223> OTHER INFORMATION: Forward primer for A10 ab CH

<400> SEQUENCE: 53
gcctccacca agggcccatc                                               20

<210> SEQ ID NO 54
<211> LENGTH: 20
<212> TYPE: DNA
<213> ORGANISM: Artificial Sequence
<220> FEATURE:
<223> OTHER INFORMATION: Reverse primer for A10 ab CH

<400> SEQUENCE: 54
gcggccgcgg tcaccaattc                                               20

<210> SEQ ID NO 55
<211> LENGTH: 36
<212> TYPE: DNA
<213> ORGANISM: Artificial Sequence
<220> FEATURE:
<223> OTHER INFORMATION: Forward primer for A10 ab VH

<400> SEQUENCE: 55
gaattggtga ccgcggccgc agagtggcca ttacgg                             36

<210> SEQ ID NO 56
<211> LENGTH: 36
<212> TYPE: DNA
<213> ORGANISM: Artificial Sequence
<220> FEATURE:
<223> OTHER INFORMATION: Reverse primer for A10 ab VH

<400> SEQUENCE: 56
gggcccttgg tggaggctgc agagacagtg accaga                             36

<210> SEQ ID NO 57
<211> LENGTH: 20
<212> TYPE: DNA
<213> ORGANISM: Artificial Sequence
<220> FEATURE:
<223> OTHER INFORMATION: Forward primer for A10 ab CL

<400> SEQUENCE: 57
cgaactgtgg ctgcaccatc                                                    20

<210> SEQ ID NO 58
<211> LENGTH: 20
<212> TYPE: DNA
<213> ORGANISM: Artificial Sequence
<220> FEATURE:
<223> OTHER INFORMATION: Reverse primer for A10 ab CL

<400> SEQUENCE: 58
gcggccgcgg tcaccaattc                                                    20

<210> SEQ ID NO 59
<211> LENGTH: 36
<212> TYPE: DNA
<213> ORGANISM: Artificial Sequence
<220> FEATURE:
<223> OTHER INFORMATION: Forward primer for A10 ab VL

<400> SEQUENCE: 59
gaattggtga ccgcggccgc agagtggcca ttacgg                                  36

<210> SEQ ID NO 60
<211> LENGTH: 41
<212> TYPE: DNA
<213> ORGANISM: Artificial Sequence
<220> FEATURE:
<223> OTHER INFORMATION: Reverse primer for A10 ab VL

<400> SEQUENCE: 60
gatggtgcag ccacagttcg tttcagctcc agcttggtcc c                            41

<210> SEQ ID NO 61
<211> LENGTH: 23
<212> TYPE: DNA
<213> ORGANISM: Artificial Sequence
<220> FEATURE:
<223> OTHER INFORMATION: Forward primer for  1G2 ab, 12D10 ab, 9A7 ab

<400> SEQUENCE: 61
aagcagtggt atcaacgcag agt                                                23

<210> SEQ ID NO 62
<211> LENGTH: 30
<212> TYPE: DNA
<213> ORGANISM: Artificial Sequence
<220> FEATURE:
<223> OTHER INFORMATION: Reverse primer for  1G2 ab, 12D10 ab

<400> SEQUENCE: 62
taggaccaga gggctccaag gacactggga                                         30

<210> SEQ ID NO 63
<211> LENGTH: 32
<212> TYPE: DNA
<213> ORGANISM: Artificial Sequence
<220> FEATURE:

-continued

```
<223> OTHER INFORMATION: Forward primer for  1G2 ab, 12D10 ab, 9A7 ab

<400> SEQUENCE: 63
ggggcggccg cagagtggcc attacggccg gg                                         32

<210> SEQ ID NO 64
<211> LENGTH: 35
<212> TYPE: DNA
<213> ORGANISM: Artificial Sequence
<220> FEATURE:
<223> OTHER INFORMATION: Reverse primer for  1G2 ab, 12D10 ab

<400> SEQUENCE: 64
ggggaattct catttaccag gagagtggga gaggc                                      35
```

ANTI-ADAMTS13 ANTIBODY AND USE THEREOF

This application is the U.S. National Phase under 35 U.S.C. § 371 of International Application PCT/JP2022/009106, filed Mar. 3, 2022, designating the U.S., and published in Japanese as WO 2022/186331 on Sep. 9, 2022, which claims priority to Japanese Patent Application No. 2021-035392, filed on Mar. 5, 2021, the entire content of which is incorporated herein by reference.

SEQUENCE LISTING STATEMENT

The present application contains a Sequence Listing, which is being submitted via Patent Center on even date herewith. The Sequence Listing is submitted in a file entitled "2024-02-14_Sequence_Listing_UIPS004_001APC.txt" which was created on Feb. 14, 2024, and is approximately 57, 344 bytes in size. This Sequence Listing is hereby incorporated by reference.

TECHNICAL FIELD

The present invention relates to an antibody having an inhibitory function against the activity of ADAMTS13, which is von Willebrand factor (VWF) cleaving protease, having activity of cleaving VWF, and pharmaceutical use of such an antibody.

BACKGROUND ART

Von Willebrand factor (VWF) is a high-molecular plasma glycoprotein having effects of initial platelet adhesion, platelet aggregation, and coagulation factor VIII stabilization at a vascular injury site. VWF is produced by vascular endothelial cells or megakaryocytes, secreted as a multimer, and cleaved into a size appropriate for a hemostatic function by ADAMTS13, VWF cleaving protease. However, the excessive cleavage of VWF by ADAMTS13 develops von Willebrand disease (VWD) which is a congenital coagulopathy causing bleeding.

The inventors of the present invention have prepared a monoclonal antibody having specific affinity for ADAMTS13 for the purpose of treating VMD (Patent Literature 1). The inventors have showed that the obtained antibody was used to exhibit localization of human ADAMTS13 in satellite cells of the liver (Non Patent Literature 1).

In recent years, the occurrence of bleeding complications after implantation of left ventricular assist device (LVAD) has become a large problem. An important factor thereof is a loss of a high-molecular-weight multimer of VWF in patients after mechanical assisted circulation (Non Patent Literature 2). In short, unlike VMD, the congenital genetic disease, this disorder is acquired von Willebrand syndrome (AVWS) which is characterized by having bleeding diathesis neither in a previous medical history nor in a family history. In the present situation, AVWS is gaining attention with increase in the number of diseases in need of mechanical assisted circulation.

However, a method for preventing or treating AVWS has not yet been established. Therefore it is an urgent issue to establish such method.

CITATION LIST

Patent Literature

Patent Literature 1: Japanese Patent No. 4533995

Non Patent Literature

Non Patent Literature 1: Uemura M, et al., Blood, 106, 922-924, 2005

Non Patent Literature 2: Meyer A L, et al., JACC Heart Fail 2141-145, 2014

SUMMARY OF INVENTION

Technical Problem

An object of the present invention is to provide a preparation of an antibody or an antibody derivative that can prevent or treat AVWS accompanied by a disease in need of mechanical assisted circulation.

Solution to Problem

The present invention has achieved the object by providing an antibody or an antibody derivative that has specific binding activity against ADAMTS13, VWF cleaving protease which is considered as a causative factor of the human AVWS, and can reduce the excessive cleavage of VWF by ADAMTS13.

More specifically, the application of this case provides the following aspects in order to attain the object mentioned above: [1] an antibody or an antibody derivative thereof having a binding property to ADAMTS13 and having an inhibitory effect on von Willebrand factor (VWF) cleaving activity, comprising any heavy chain and light chain complementarity determining regions selected from the group consisting of (1) heavy chain complementarity determining regions CDR1 (GYSFTGYT, SEQ ID NO: 1), CDR2 (INPYNGGT, SEQ ID NO: 2), and CDR3 (ARTSGYLFAY, SEQ ID NO: 3), and light chain complementarity determining regions CDR1 (EDIYNR, SEQ ID NO: 4), CDR2 (GAT, SEQ ID NO: 5), and CDR3 (QQYWSSPLT, SEQ ID NO: 6);

(2) heavy chain complementarity determining regions CDR1 (GFSLPRYG, SEQ ID NO: 7), CDR2 (IWAGGST, SEQ ID NO: 8), and CDR3 (ARAGGSOPFDY, SEQ ID NO: 9), and light chain complementarity determining regions CDR1 (RDINTY, SEQ ID NO: 10), CDR2 (RAN, SEQ ID NO: 11), and CDR3 (LOYDEFPWT, SEQ ID NO: 12);

(3) heavy chain complementarity determining regions CDR1 (GFSLTRYG, SEQ ID NO: 13), CDR2 (IWAGGST, SEQ ID NO: 14), and CDR3 (ARAGGSSSFDY, SEQ ID NO: 15), and light chain complementarity determining regions CDR1 (QDINTY, SEQ ID NO: 16), CDR2 (RAN, SEQ ID NO: 17), and CDR3 (LOYDEFPWT, SEQ ID NO: 18); and (4) heavy chain complementarity determining regions CDR1 (GFSLTGYG, SEQ ID NO: 19), CDR2 (IWADGTT, SEQ ID NO: 20), and CDR3 (ARAGGSQPFDY, SEQ ID NO: 21), and light chain complementarity determining regions CDR1 (QDINSY, SEQ ID NO: 22), CDR2 (RAN, SEQ ID NO: 23), and CDR3 (LOYDEFPWT, SEQ ID NO: 24);

[2] the antibody or the antibody derivative according to [1], wherein the antibody or the antibody derivative is of recombinant type;

[3] the antibody or the antibody derivative according to [1] or [2], wherein the antibody derivative is selected from an engineered antibody selected from the group consisting of a humanized antibody, a chimeric antibody, a single-chain antibody, a multivalent antibody, and a multispecific antibody, or a functional fragment thereof;

[4] the antibody or the antibody derivative according to any of [1] to [3], wherein an amino acid sequence of a heavy chain variable region VH domain of the antibody or the antibody derivative is selected from the group consisting of (1-1) the amino acid sequence of SEQ ID NO: 25, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 25, (1-2) the amino acid sequence of SEQ ID NO: 27, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 27, (1-3) the amino acid sequence of SEQ ID NO: 29, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 29, (2) the amino acid sequence of SEQ ID NO: 31, or an amino acid sequence having the substitution (e.g., conservative substitution), insertion, or deletion of one or several amino acids at a moiety except for CDR1 (SEQ ID NO: 7), CDR2 (SEQ ID NO: 8), and CDR3 (SEQ ID NO: 9) in the amino acid sequence of SEQ ID NO: 31, (3) the amino acid sequence of SEQ ID NO: 33, or an amino acid sequence having the substitution (e.g., conservative substitution), insertion, or deletion of one or several amino acids at a moiety except for CDR1 (SEQ ID NO: 13), CDR2 (SEQ ID NO: 14), and CDR3 (SEQ ID NO: 15) in the amino acid sequence of SEQ ID NO: 33, and (4) the amino acid sequence of SEQ ID NO: 35, or an amino acid sequence having the substitution (e.g., conservative substitution), insertion, or deletion of one or several amino acids at a moiety except for CDR1 (SEQ ID NO: 19), CDR2 (SEQ ID NO: 20), and CDR3 (SEQ ID NO: 21) in the amino acid sequence of SEQ ID NO: 35;

[5] the antibody or the antibody derivative according to any of [1] to [4], wherein an amino acid sequence of a light chain variable region VL domain of the antibody or the antibody derivative is selected from the group consisting of (1-1) the amino acid sequence of SEQ ID NO: 26, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 26, (1-2) the amino acid sequence of SEQ ID NO: 28, or an amino acid sequence having the substitution (e.g., conservative substitution), insertion, or deletion of one or several amino acids at a moiety except for CDR1

(SEQ ID NO: 4), CDR2 (SEQ ID NO: 5), and CDR3 (SEQ ID NO: 6) in the amino acid sequence of SEQ ID NO: 28, (1-3) the amino acid sequence of SEQ ID NO: 30, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 30, (2) the amino acid sequence of SEQ ID NO: 32, or an amino acid sequence having the substitution (e.g., conservative substitution), insertion, or deletion of one or several amino acids at a moiety except for CDR1 (SEQ ID NO: 10), CDR2 (SEQ ID NO: 11), and CDR3 (SEQ ID NO: 12) in the amino acid sequence of SEQ ID NO: 32, (3) the amino acid sequence of SEQ ID NO: 34, or an amino acid sequence having the substitution (e.g., conservative substitution), insertion, or deletion of one or several amino acids at a moiety except for CDR1 (SEQ ID NO: 16), CDR2 (SEQ ID NO: 17), and CDR3 (SEQ ID NO: 18) in the amino acid sequence of SEQ ID NO: 34, and (4) the amino acid sequence of SEQ ID NO: 36, or an amino acid sequence having the substitution (e.g., conservative substitution), insertion, or deletion of one or several amino acids at a moiety except for CDR1 (SEQ ID NO: 22), CDR2 (SEQ ID NO: 23), and CDR3 (SEQ ID NO: 24) in the amino acid sequence of SEQ ID NO: 36;

[6] the antibody or the antibody derivative according to any of [1] to [5], wherein the antibody or the antibody derivative is selected from the group consisting of (1-1) an antibody or an antibody derivative comprising
a heavy chain (the amino acid sequence of SEQ ID NO: 37, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 37) and
a light chain (the amino acid sequence of SEQ ID NO: 38, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 38);

(1-2) a heavy chain (the amino acid sequence of SEQ ID NO: 39, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 39) and
a light chain (the amino acid sequence of SEQ ID NO: 40, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 40);

(1-3) a heavy chain (the amino acid sequence of SEQ ID NO: 41, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 41) and a light chain (the amino acid sequence of SEQ ID NO: 42, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 42);

(2) an antibody or an antibody derivative comprising a heavy chain (the amino acid sequence of SEQ ID NO: 43, or an amino acid sequence having the substitution (e.g., conservative substitution), insertion, or deletion of one or several amino acids at a moiety except for CDR1 (SEQ ID NO: 7), CDR2 (SEQ ID NO: 8), and CDR3 (SEQ ID NO: 9) in the amino acid sequence of SEQ ID NO: 43) and a light chain (the amino acid sequence of SEQ ID NO: 44, or an amino acid sequence having the substitution (e.g., conservative substitution), insertion, or deletion of one or several amino acids at a moiety except for CDR1 (SEQ ID NO: 10), CDR2 (SEQ ID NO: 11), and CDR3 (SEQ ID NO: 12) in the amino acid sequence of SEQ ID NO: 44);

(3) an antibody or an antibody derivative comprising a heavy chain (the amino acid sequence of SEQ ID NO: 45, or an amino acid sequence having the substitution (e.g., conservative substitution), insertion, or deletion of one or several amino acids at a moiety except for CDR1 (SEQ ID NO: 13), CDR2 (SEQ ID NO: 14), and CDR3 (SEQ ID NO: 15) in the amino acid sequence of SEQ ID NO: 45) and a light chain (the amino acid sequence of SEQ ID NO: 46, or an amino acid sequence having the substitution (e.g., conservative substitution), insertion, or deletion of one or several amino acids at a moiety except for CDR1 (SEQ ID NO: 16), CDR2 (SEQ ID NO: 17), and CDR3 (SEQ ID NO: 18) in the amino acid sequence of SEQ ID NO: 46); and (4) an antibody or an antibody derivative comprising a heavy chain (the amino acid sequence of SEQ ID NO: 47, or an amino acid sequence having the substitution (e.g., conservative substitution), insertion, or deletion of one or several amino acids at a moiety except for CDR1 (SEQ ID NO: 19), CDR2 (SEQ ID NO: 20), and CDR3 (SEQ ID NO: 21) in the amino acid sequence of SEQ ID NO: 47) and a light chain (the amino acid sequence of SEQ ID NO: 48, or an amino acid sequence having the substitution (e.g., conservative substitution), insertion, or deletion of one or several amino acids at a moiety except for CDR1 (SEQ ID NO: 22), CDR2 (SEQ ID NO: 23), and CDR3 (SEQ ID NO: 24) in the amino acid sequence of SEQ ID NO: 48);

[7] a pharmaceutical composition for preventing or treating bleeding caused by the excessive cleavage of VWF, comprising the antibody or the antibody derivative according to any one of claims 1 to 6;

[8] the pharmaceutical composition according to [7], wherein the bleeding caused by the excessive cleavage of VWF is bleeding associated with mechanical assisted circulation;

[9] the pharmaceutical composition according to [7] or [8], wherein the pharmaceutical composition comprises plural types of antibodies or antibody derivatives according to any of [1] to [6];

[10] the pharmaceutical composition according to any of [7] to [9], wherein the pharmaceutical composition inhibits the cleaving activity of ADAMTS13 against VWF;

[11] the pharmaceutical composition according to any of [7] to [10], wherein the bleeding associated with mechanical assisted circulation is acquired von Willebrand syndrome (AVWS);

[12] the pharmaceutical composition according to any of [7] to [11], wherein the mechanical assisted circulation is selected from the group consisting of extracorporeal membrane oxygenation (ECMO), implantable left ventricular assist device (LVAD), and percutaneous cardiopulmonary support (PCPS);

[13] a method for detecting and/or measuring the presence or an amount of ADAMTS13 in a biological sample, comprising the steps of:

contacting the biological sample collected from a test subject with the antibody or the antibody derivative according to any of [1] to [6] in vitro; and detecting and/or measuring ADAMTS13 in the sample bound with the antibody or the antibody derivative;

[14] a kit for detecting and/or measuring the presence or an amount of ADAMTS13 in the body of a test subject, comprising the antibody or the antibody derivative according to any of [1] to [6];

[15] a method for detecting and/or measuring the VWF cleaving activity of ADAMTS13 in a biological sample, comprising the steps of:

adding varying concentrations of the antibody or the antibody derivative according to any of [1] to [6] to the biological sample collected from a test subject, followed by incubation; and detecting and/or measuring an intact VWF multimer, an intact VWF monomer, or a cleaved VWF fragment in the sample; and

[16] a kit for detecting and/or measuring an intact VWF multimer, an intact VWF monomer, or a cleaved VWF fragment in the body of a test subject, comprising the antibody or the antibody derivative according to any of [1] to [6].

Advantageous Effects of Invention

The present invention can provide an antibody or an antibody derivative that has specific binding activity against ADAMTS13, von Willebrand factor (VWF) cleaving protease which is considered as a causative factor of the acquired von Willebrand syndrome (AVWS) in humans, and can reduce the excessive cleavage of VWF by ADAMTS13. Since the excessive cleavage of VWF by ADAMTS13 is considered as pathogenesis of the acquired von Willebrand syndrome (AVWS) in humans, the present invention can also provide a pharmaceutical composition for preventing or treating human AVWS, comprising the antibody or the antibody derivative of the present invention.

DESCRIPTION OF EMBODIMENTS

Terms used in the present invention are defined as follows:

(a) Von Willebrand Factor (VWF)

VWF is a high-molecular plasma glycoprotein having effects of initial platelet adhesion at a vascular injury site, platelet aggregation, and coagulation factor VIII stabilization. VWF is produced by vascular endothelial cells or megakaryocytes, secreted as a multimer, and cleaved into a size appropriate for a hemostatic function by ADAMTS13, a VWF cleaving enzyme.

(b) von Willebrand disease (VWD) is a congenital coagulopathy leading to bleeding tendency due to quantitative and qualitative abnormalities of VWF. VWD is classified into 6 types, type 1, type 2A, type 2B, type 2M, type 2N, and type 3. VWD frequently causes bleeding symptoms suggestive of impaired platelet aggregation (nose bleeding, purpura/subcutaneous hematoma, oral mucosal bleeding, hypermenorrhea, etc.).

(c) Acquired von Willebrand syndrome (AVWS) is a relatively rare acquired coagulopathy that assumes a pathological condition similar to that of congenital VWD in association with a pre-existing disease (lymphoproliferative disease, autoimmune disease, myeloproliferative disease, cardiovascular disease, malignant tumor, hypothyroidism, etc.), and is characterized by having bleeding diathesis neither in a previous medical history nor in a family history.

The present invention demonstrates that the object of the present invention can be achieved by providing an antibody or an antibody derivative having a binding property to ADAMTS13 and having an inhibitory effect on VWF cleaving activity, which comprises heavy chain and light chain complementarity determining regions having particular amino acid sequences.

Target Antigen

Figure 1:
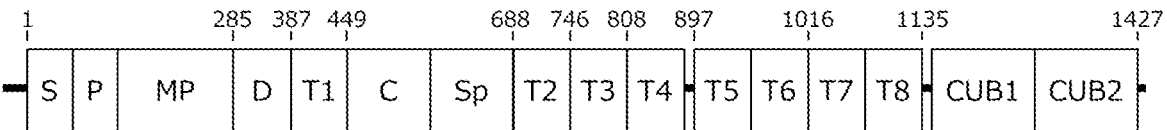
FIG. 1 is a figure showing the domain structure of ADAMTS13 which is a target substance of the antibody or the antibody derivative of the present invention. The numerals in the drawing represent amino acid numbers.

ADAMTS13 serving as a target antigen of the antibody or the antibody derivative of the present invention is an enzyme protein constituted by 1427 amino acids (GenBank No: AY055376) and has a molecular weight of approximately 200 KDa. A primary structure thereof consists of a multidomain containing a signal peptide(S), a propeptide (P), a metalloprotease domain (MP), a disintegrin-like domain (D), a thrombospondin-1 motif (T1), a cysteine-rich domain (C), a spacer domain(S), and seven repeat structures of the thrombospondin-1-motif (T2 to T8), and finally two CUB domains (CUB1 and CUB2) in order from the N-terminal side (see, FIG. 1). A physiological substrate of ADAMTS13 known in the art is only VWF, and the MDTCS domain (domain consisting of the MP domain, the D domain, the T1 domain, the C domain, and the Sp domain) of ADAMTS13 is necessary for the cleavage of VWF.

The antibody or the antibody derivative of the present invention may target any moiety in this domain structure. Examples of the antibody or the antibody derivative include: an antibody or an antibody derivative which binds to a partial amino acid sequence of the MDTCS domain as an epitope by targeting the MDTCS domain itself which is essential for the VWF cleaving activity mentioned above, wherein the antibody or the antibody derivative binds to the cleaving function domain of ADAMTS13 to block its function; and an antibody or an antibody derivative that binds to a moiety other than the MDTCS domain and conformationally prevents ADAMTS13 from binding to VWF as a result of binding to the moiety other than the MDTCS domain.

Antibody or Antibody Derivative

In one aspect, the present invention provides an antibody or an antibody derivative thereof having a binding property to ADAMTS13 and having an inhibitory effect on VWF cleaving activity, comprising particular heavy chain and light chain complementarity determining regions (CDRs), or heavy chain and light chain variable regions comprising these CDRs or a heavy chain and a light chain comprising these CDRs.

The antibody or the antibody derivative used in the present invention is preferably free of a pathogen, such as a virus (e.g., HBV, hepatitis C virus (HCV), and human immunodeficiency virus (HIV)), which might be contained in blood (or which has the risk of contaminating blood preparations), and free of a blood-derived component having the risk of causing an immune abnormality in recipient individuals, such as an antigenic protein contained in blood or an antibody that binds to a human protein, in order to circumvent various problems (particularly, infection problems and immunity problems) peculiar to blood preparations such as blood-derived antibody preparations.

For example, the present invention can provides an antibody prepared by obtaining immortalized cells derived from antibody-producing cells under blood-derived component-free conditions and preparing the antibody from the cells under blood-derived component-free culture conditions, or a recombinant antibody that can be prepared by recombinantly expressing an antibody protein using DNA that encodes the antibody protein prepared from the immortalized cells as the antibody free of a blood-derived component.

Specifically, in one aspect, the antibody according to the present invention can be prepared by obtaining and immortalizing cell clones that produce an antibody having a binding property to ADAMTS13 from the blood of an individual administered with the whole or a portion of ADAMTS13 as a target antigen, to obtain immortalized cells derived from the antibody-producing cells, and selecting cells that produce an antibody having inhibitory activity on the VWF cleaving function of ADAMTS13 from the immortalized antibody-producing cells.

In another aspect, the present invention can also provide an antibody of recombinant type that binds to ADAMTS13 and has activity of inhibiting the VWF cleaving function of ADAMTS13 by use of a genetic recombination technique. More specifically, the present invention can also provide, as the antibody of the present invention, a monoclonal antibody having the activity of interest obtained by: in accordance with a well-known method, acquiring mRNA from immortalized antibody-producing cells selected by the method described above that produce an antibody having activity of inhibiting the VWF cleaving function of ADAMTS13, preparing cDNA from the mRNA, and obtaining a DNA sequence that encodes the antibody protein; and expressing the DNA sequence encoding the antibody in a blood-derived component-free mammalian expression system using a vector to produce a recombinant immunoglobulin (IgG).

In the present invention, a derivative of such an antibody can be used. The antibody derivative that can be used in the present invention can be, for example, but not limited to, an engineered antibody selected from the group consisting of a humanized antibody, a chimeric antibody, a single-chain antibody, a multivalent antibody, and a multispecific antibody, or a functional fragment thereof. Among them, the functional fragment that can be used is, for example, but not limited to, F(ab')2.

Such a derivative of the antibody can be prepared in accordance with a method well known in the art after production of the antibody, and can be prepared as a recombinant antibody derivative described about the antibody of the present invention mentioned above.

The antibody or the antibody derivative prepared by the method mentioned above has a binding property to ADAMTS13. The present invention provides an antibody or an antibody derivative having inhibitory activity on the VWF cleaving function of ADAMTS13 by further screening out the antibody having the inhibitory effect among the antibodies or antibody derivatives having a binding property to ADAMTS13.

In this aspect, the particular heavy chain and light chain complementarity determining regions (CDRs) contained in the antibody or the antibody derivative of the present invention targeted to ADAMTS13 can be selected from the group consisting of the following (1) to (4):

(1) heavy chain complementarity determining regions CDR1 (GYSFTGYT, SEQ ID NO: 1), CDR2 (INPYN-GGT, SEQ ID NO: 2), and CDR3 (ARTSGYLFAY, SEQ ID NO: 3), and light chain complementarity determining regions CDR1 (EDIYNR, SEQ ID NO: 4), CDR2 (GAT, SEQ ID NO: 5), and CDR3 (QQYWSSPLT, SEQ ID NO: 6);

(2) heavy chain complementarity determining regions CDR1 (GFSLPRYG, SEQ ID NO: 7), CDR2 (IWAGGST, SEQ ID NO: 8), and CDR3 (ARAGGSOPFDY, SEQ ID NO: 9), and light chain complementarity determining regions CDR1 (RDINTY, SEQ ID NO: 10), CDR2 (RAN, SEQ ID NO: 11), and CDR3 (LOYDEFPWT, SEQ ID NO: 12);

(3) heavy chain complementarity determining regions CDR1 (GFSLTRYG, SEQ ID NO: 13), CDR2 (IWAGGST, SEQ ID NO: 14), and CDR3 (ARAGGSSSFDY, SEQ ID NO: 15), and light chain complementarity determining regions CDR1 (QDINTY, SEQ ID NO: 16), CDR2 (RAN, SEQ ID NO: 17), and CDR3 (LQYDEFPWT, SEQ ID NO: 18); and (4) heavy chain complementarity determining regions CDR1 (GFSLTGYG, SEQ ID NO: 19), CDR2 (IWADGTT, SEQ ID NO: 20), and CDR3 (ARAGGSQPFDY, SEQ ID NO: 21), and light chain complementarity determining regions CDR1 (QDINSY, SEQ ID NO: 22), CDR2 (RAN, SEQ ID NO: 23), and CDR3 (LOYDEFPWT, SEQ ID NO: 24).

In this aspect, the amino acid sequence of a particular heavy chain variable region VH domain contained in the antibody or the antibody derivative of the present invention targeted to ADAMTS13 can be selected from the group consisting of:

(1-1) the amino acid sequence of SEQ ID NO: 25, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 25, (1-2) the amino acid sequence of SEQ ID NO: 27, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 27, (1-3) the amino acid sequence of SEQ ID NO: 29, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 29, (2) the amino acid sequence of SEQ ID NO: 31, or an amino acid sequence having the substitution (e.g., conservative substitution), insertion, or deletion of one or several amino acids at a moiety except for CDR1 (SEQ ID NO: 7), CDR2 (SEQ ID NO: 8), and CDR3 (SEQ ID NO: 9) in the amino acid sequence of SEQ ID NO: 31, (3) the amino acid sequence of SEQ ID NO: 33, or an amino acid sequence having the substitution (e.g., conservative substitution), insertion, or deletion of one or several amino acids at a moiety except for CDR1 (SEQ ID NO: 13), CDR2 (SEQ ID NO: 14), and CDR3 (SEQ ID NO: 15) in the amino acid sequence of SEQ ID NO: 33, and (4) the amino acid sequence of SEQ ID NO: 35, or an amino acid sequence having the substitution (e.g., conservative substitution), insertion, or deletion of one or several amino acids at a moiety except for CDR1 (SEQ ID NO: 19), CDR2 (SEQ ID NO: 20), and CDR3 (SEQ ID NO: 21) in the amino acid sequence of SEQ ID NO: 35.

In this case, the amino acid sequence of an existing antibody can be used as the amino acid sequence of a heavy chain constant region CH domain. For example, the amino acid sequence of a CH domain of any human antibody or an amino acid sequence engineered from such an amino acid sequence can be used. Specifically, on the basis of the technical knowledge that CDR1 to CDR3 in the amino acid sequence of each heavy chain constant region CH domain are essential for binding to a target antigen, the present invention can provide the antibody or the antibody derivative thereof as long as an amino acid sequence having the substitution (e.g., conservative substitution), insertion, or deletion of one or several amino acids at a moiety except for CDR1 to CDR3 can constitute the antibody or the antibody derivative thereof having a binding property to ADAMTS13 and having an inhibitory effect on von Willebrand factor (VWF) cleaving activity.

In this aspect, the amino acid sequence of a particular light chain variable region VL domain contained in the antibody or the antibody derivative of the present invention targeted to ADAMTS13 can be selected from the group consisting of (1-1) the amino acid sequence of SEQ ID NO: 26, or an amino acid sequence having the substitution (e.g., conservative substitution), insertion, or deletion of one or several amino acids at a moiety except for CDR1

(SEQ ID NO: 4), CDR2 (SEQ ID NO: 5), and CDR3 (SEQ ID NO: 6) in the amino acid sequence of SEQ ID NO: 26, (1-2) the amino acid sequence of SEQ ID NO: 28, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 28, (1-3) the amino acid sequence of SEQ ID NO: 30, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 30, (2) the amino acid sequence of SEQ ID NO: 32, or an amino acid sequence having the substitution (e.g., conservative substitution), insertion, or deletion of one or several amino acids at a moiety except for CDR1 (SEQ ID NO: 10), CDR2 (SEQ ID NO: 11), and CDR3 (SEQ ID NO: 12) in the amino acid sequence of SEQ ID NO: 32, (3) the amino acid sequence of SEQ ID NO: 34, or an amino acid sequence having the substitution (e.g., conservative substitution), insertion, or deletion of one or several amino acids at a moiety except for CDR1 (SEQ ID NO: 16), CDR2 (SEQ ID NO: 17), and CDR3 (SEQ ID NO: 18) in the amino acid sequence of SEQ ID NO: 34, and (4) the amino acid sequence of SEQ ID NO: 36, or an amino acid sequence having the substitution (e.g., conservative substitution), insertion, or deletion of one or several amino acids at a moiety except for CDR1 (SEQ ID NO: 22), CDR2 (SEQ ID NO: 23), and CDR3 (SEQ ID NO: 24) in the amino acid sequence of SEQ ID NO: 36.

In this case, the amino acid sequence of an existing antibody can be used as the amino acid sequence of a light chain constant region CL domain. For example, the amino acid sequence of a CL domain of any human antibody or an amino acid sequence engineered from such an amino acid sequence can be used. Specifically, on the basis of the technical knowledge that CDR1 to CDR3 in the amino acid sequence of each light chain constant region CL domain are essential for binding to a target antigen, the present invention can provide the antibody or the antibody derivative thereof as long as an amino acid sequence having the substitution (e.g., conservative substitution), insertion, or deletion of one or several amino acids at a moiety except for CDR1 to CDR3 can constitute the antibody or the antibody derivative thereof having a binding property to ADAMTS13 and having an inhibitory effect on von Willebrand factor (VWF) cleaving activity.

In this aspect, the particular heavy chain and light chain contained in the antibody or the antibody derivative of the present invention targeted to ADAMTS13 can be selected from the group consisting of the following (1-1) to (4):

(1-1) a heavy chain (the amino acid sequence of SEQ ID NO: 37, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 37) and a light chain (the amino acid sequence of SEQ ID NO: 38, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 38);

(1-2) a heavy chain (the amino acid sequence of SEQ ID NO: 39, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 39) and a light chain (the amino acid sequence of SEQ ID NO: 40, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 40);

(1-3) a heavy chain (the amino acid sequence of SEQ ID NO: 41, or an amino acid sequence having the substitution (e.g., conservative substitution), insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 41) and a light chain (the amino acid sequence of SEQ ID NO: 42, or an amino acid sequence having the substitution (e.g., conservative substitution), insertion, or deletion of one or several amino acids at a moiety except for CDR1 (SEQ ID NO: 4), CDR2 (SEQ ID NO: 5), and CDR3 (SEQ ID NO: 6) in the amino acid sequence of SEQ ID NO: 42);

(2) a heavy chain (the amino acid sequence of SEQ ID NO: 43, or an amino acid sequence having the substitution (e.g., conservative substitution), insertion, or deletion of one or several amino acids at a moiety except for CDR1 (SEQ ID NO: 7), CDR2 (SEQ ID NO: 8), and CDR3 (SEQ ID NO: 9) in the amino acid sequence of SEQ ID NO: 43) and a light chain (the amino acid sequence of SEQ ID NO: 44, or an amino acid sequence having the substitution (e.g., conservative substitution), insertion, or deletion of one or several amino acids at a moiety except for CDR1 (SEQ ID NO: 10), CDR2 (SEQ ID NO: 11), and CDR3 (SEQ ID NO: 12) in the amino acid sequence of SEQ ID NO: 44);

(3) a heavy chain (the amino acid sequence of SEQ ID NO: 45, or an amino acid sequence having the substitution (e.g., conservative substitution), insertion, or deletion of one or several amino acids at a moiety except for CDR1 (SEQ ID NO: 13), CDR2 (SEQ ID NO: 14), and CDR3 (SEQ ID NO: 15) in the amino acid sequence of SEQ ID NO: 45) and a light chain (the amino acid sequence of SEQ ID NO: 46, or an amino acid sequence having the substitution (e.g., conservative substitution), insertion, or deletion of one or several amino acids at a moiety except for CDR1 (SEQ ID NO: 16), CDR2 (SEQ ID NO: 17), and CDR3 (SEQ ID NO: 18) in the amino acid sequence of SEQ ID NO: 46); and (4) a heavy chain (the amino acid sequence of SEQ ID NO: 47, or an amino acid sequence having the substitution (e.g., conservative substitution), insertion, or deletion of one or several amino acids at a moiety except for CDR1 (SEQ ID NO: 19), CDR2 (SEQ ID NO: 20), and CDR3 (SEQ ID NO: 21) in the amino acid sequence of SEQ ID NO: 47) and a light chain (the amino acid sequence of SEQ ID NO: 48, or an amino acid sequence having the substitution (e.g., conservative substitution), insertion, or deletion of one or several amino acids at a moiety except for CDR1 (SEQ ID NO: 22), CDR2 (SEQ ID NO: 23), and CDR3 (SEQ ID NO: 24) in the amino acid sequence of SEQ ID NO: 48).

In this case, on the basis of the technical knowledge that, for a heavy chain and a light chain, CDR1 to CDR3 in each of the amino acid sequences of the heavy chain and the light chain are essential for binding to a target antigen, the present invention can provide the antibody or the antibody derivative thereof as long as an amino acid sequence having the substitution (e.g., conservative substitution), insertion, or deletion of one or several amino acids at a moiety except for CDR1 to CDR3 can constitute the antibody or the antibody derivative thereof having a binding property to ADAMTS13 and having an inhibitory effect on von Willebrand factor (VWF) cleaving activity.

Inhibitory effect of the antibody or the antibody derivative on VWF cleaving activity of ADAMTS13

VWF has a cleavage site by ADAMTS13 at $Tyr^{1605}$-$Met^{1606}$ of its A2 domain and assumes a structure that does not permit an access of ADAMTS13 to the cleavage site because this cleavage site is embedded within the A2 domain when it is present as a multimer in plasma. On the other hand, when a portion of the VWF multimer binds to a vascular endothelial cell, platelet, or the like and a physical force caused by blood flow or the like is applied thereto, the structure of the A2 domain is changed so that ADAMTS13 can access to the cleavage site in the A2 domain of VWF. In such a case, ADAMTS13 functions as metalloprotease that specifically cleaves the higher order structure of the multimer.

A feature of the antibody or the antibody derivative of the present invention is to have an inhibitory effect on the VWF cleaving activity of ADAMTS13 described above. Whether the antibody or the antibody derivative has an inhibitory effect on the VWF cleaving activity of ADAMTS13 can be screened by, for example, confirming by Western blot that the cleavage of VWF is inhibited. The screening by Western blot can be performed in vitro by mixing a prescribed amount of monomer VWF with a prescribed amount of ADAMTS13, adding thereto the subject antibody to be evaluated at varying concentrations, and detecting change in the amount of VWF cleaved in an antibody concentration-dependent manner by Western blot.

Medical Use

Since a VWF multimer having a larger molecular weight has higher ability to aggregate platelet, its cleavage by ADAMTS13 (i.e., decreasing in its molecular weight) suppresses VWF-dependent platelet aggregation. Therefore, if VWF is excessively cleaved due to increased ADAMTS13 activity, platelet aggregation is excessively suppressed, causing bleeding tendency which may cause congenital VWD or acquired AVWS. On the other hand, insufficient ADAMTS13 activity may cause excessive platelet aggregation. In a living body in a normal state, the cleavage of a VWF multimer by ADAMTS13 always occurs at a constant rate, and the balance is maintained so as not to cause bleeding and not to cause abnormal blood coagulation reaction.

The antibody or the antibody derivative of the present invention can intervene in bleeding caused by the excessive cleavage of VWF due to increased ADAMTS13 activity, because the antibody or the antibody derivative has an inhibitory effect on the VWF cleaving activity of ADAMTS13, as mentioned above. Thus, in another aspect, the present invention can provide a pharmaceutical composition for preventing or treating bleeding caused by the excessive cleavage of VWF, comprising the antibody or the antibody derivative of the present invention.

The pharmaceutical composition according to this aspect may comprise one kind of antibody or antibody derivative of the present invention or plural kinds of antibodies or antibody derivatives of the present invention as an active ingredient.

This pharmaceutical composition can exert the medical use of interest in preventing or treating bleeding caused by the excessive cleavage of VWF, by the fact that the antibody or the antibody derivative of the present invention contained as an active ingredient can inhibit the cleaving activity of ADAMTS13 against VWF.

The bleeding caused by the excessive cleavage of VWF which is a symptom to be treated by application of the pharmaceutical composition of the present invention may result from a congenital etiology or an acquired etiology and is selected from the group consisting of, for example, bleeding associated with mechanical assisted circulation and anemia.

Figure 2:
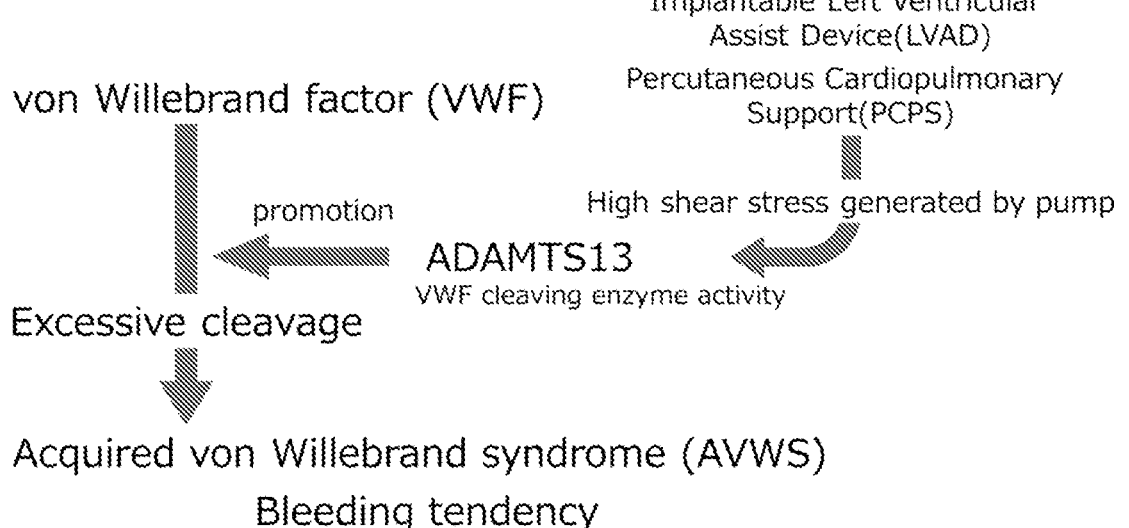
FIG. 2 is a figure showing the pathogenesis of AVWS.

AVWS can be listed as examples of the causative disease for the bleeding associated with mechanical assisted circulation mentioned above which is a symptom to be treated by application of the pharmaceutical composition of the present invention. The pathogenesis of AVWS is as shown in FIG. 2. It is considered that the structure of a VWF multimer is changed by high shear stress generated in a pump of an apparatus when mechanical assisted circulation such as extracorporeal membrane oxygenation (ECMO), implantable left ventricular assist device (LVAD), or percutaneous cardiopulmonary support (PCPS) is used. This change of the structure of a VWF multimer is considered to trigger the excessive degradation of VWF factor by ADAMTS13.

Thus, the mechanical assisted circulation when high shear stress is generated in a pump of an apparatus is an example, but not limited to, of the mechanical assisted circulation as the cause of AVWS of the present invention to be treated by the pharmaceutical composition of the present invention. Examples of such mechanical assisted circulation can include the mechanical assisted circulation selected from the group consisting of extracorporeal membrane oxygenation (ECMO), implantable left ventricular assist device (LVAD), and percutaneous cardiopulmonary support (PCPS).

Additional use of the antibody or the antibody derivative

The antibody or the antibody derivative of the present invention can also be used for other use and can be used, for example, for detecting and/or measuring the presence or an amount of ADAMTS13 and for detecting and/or measuring the VWF cleaving activity of ADAMTS13.

For the use in detecting and/or measuring ADAMTS13, the presence or an amount of ADAMTS13 in a biological sample can be detected and/or measured by the steps of:

contacting the biological sample collected from a test subject with the antibody or the antibody derivative of the present invention in vitro; and detecting and/or measuring ADAMTS13 in the sample bound with the antibody or the antibody derivative.

In this method, when ADAMTS13 is detected and/or measured, a detectable label is attached directly or indirectly to the antibody or the antibody derivative of the present invention, and the presence or an amount of ADAMTS13 can be detected and/or measured by use of an approach known in the art such as ELISA or Western blot.

The present invention can also provide a kit for detecting and/or measuring the presence or an amount of ADAMTS13, comprising the antibody or the antibody derivative of the present invention for detecting and/or measuring the presence or an amount of ADAMTS13 in a biological sample of a test subject through the use of the method described above. It is a feature of this kit to contain the antibody or the antibody derivative of the present invention as a primary antibody for detection in a general kit configuration that is used for performing ELISA, Western blot, or the like.

In this kit, in the case where the antibody or the antibody derivative of the present invention is indirectly detected using a label for detection attached, the kit may comprise a labeled secondary antibody for detecting the antibody or the antibody derivative of the present invention.

For the use in detecting and/or measuring the VWF cleaving activity of ADAMTS13, the VWF cleaving activity of ADAMTS13 in a biological sample can be detected and/or measured by the steps of:

adding varying concentrations of the antibody or the antibody derivative of the present invention to the biological sample collected from a test subject, followed by incubation for a given time; and detecting and/or measuring an intact VWF multimer, an intact VWF monomer, or a cleaved VWF fragment in the sample. It is possible to determine, by the addition of the antibody or the antibody derivative of the present invention, whether the cleavage of VWF that occurs in the absence of the antibody or the antibody derivative is cleavage caused by ADAMTS13 and whether the excessive cleavage of VWF by ADAMTS13 occurs in vivo in a test subject. In this method, in the case where an intact VWF multimer, an intact VWF monomer, or a cleaved VWF fragment is detected and/or measured, the intact VWF multimer, the intact VWF monomer, or the cleaved VWF fragment can be detected and/or measured by use of an approach known in the art such as Western blot or chromatography.

The present invention can also provide a kit for detecting and/or measuring an intact VWF multimer, an intact VWF monomer, or a cleaved VWF fragment, comprising the antibody or the antibody derivative of the present invention for detecting and/or measuring the VWF cleaving activity of ADAMTS13 in a biological sample of a test subject through the use of the method described above. It is a feature of this kit to add the antibody or the antibody derivative of the present invention for inhibiting the function of ADAMTS13 to a general kit configuration that is used for performing Western blot, chromatography, or the like.

Hereinafter, the present invention will be specifically described with reference to Examples. Examples given below do not limit the present invention by any means.

EXAMPLES

Example 1: Preparation of Antibody

This Example was performed for obtaining an antibody against ADAMTS13 produced in a mouse as a monoclonal antibody as a result of administering ADAMTS13 as an immunogen to the mouse.

(1) Antibody Preparation by Hybridoma Method

A mouse (BALB/cAJcl, 7 weeks old female, CLEA Japan, Inc.) was immunized by the intraperitoneal administration of 20 μg (microgram) of a full-length recombinant ADAMTS13 antigen (in-house preparation) together with 20 μg (microgram) of a Freund's complete adjuvant (manufactured by Difco Laboratories, Inc.) five times every two weeks. One months later, the ADAMTS13 antigen was boosted to the mouse. Two weeks later, blood was collected from the tail vein, and increase in an antibody titer in the blood specific for ADAMTS13 was confirmed by ELISA based on a conventional method. The ADAMTS13 antigen from the tail vein was further boosted to the mouse having an increased antibody titer for final immunization. Three days later, the spleen was recovered from the mouse.

A single cell suspension of spleen cells was prepared from the spleen in accordance with a method known in the art, which was fused with a 2-amino-6-mercaptopurine (6-thioguanine)-resistant BALB/c mouse-derived cultured myeloma cell line (P3-X63-Ag8.653; hereinafter, also referred to as X63 cells) as a parent cell line in accordance with a method generally used in the art.

Then, the obtained fused cells were cultured in a culture medium supplemented with a HAT selection solution, to conduct cloning. Two or three weeks later, clones that produced the anti-ADAMTS13 monoclonal antibody of interest were screened by ELISA using a microplate adsorbed with the ADAMTS13 antigen on a solid phase.

(2) Screening

A culture supernatant of the hybridoma cells was used in reaction with an ADAMTS13 antigen-immobilized ELISA plate to screen the antibody of interest. In this screening, clones that specifically reacted only with the ADAMTS13 antigen were selected by removing nonspecific reactive clones that reacted with a nonspecific oligopeptide-immobilized ELISA plate.

The hybridoma cell line that specifically reacted with an ADAMTS13 antigen-immobilized ELISA plate was selected and then cloned by the limiting dilution method to obtain A10 antibody as an anti-monoclonal antibody from the hybridomas.

Example 2: Preparation of Another Antibody

This Example was performed for obtaining another new antibody against ADAMTS13 as a monoclonal antibody, in addition to the antibody obtained in Example 1.

(1) Antibody Preparation by Hybridoma Method

A mouse (BALB/cA, 7 weeks old female, Japan SLC, Inc.) was immunized by the footpad injection of 20 μg (microgram) of a recombinant antigen of an ADAMTS13 metalloprotease domain (MP) linked with a disintegrin-like domain (D) (MP domain+D domain; hereinafter, referred to as an "ADAMTS13 MD recombinant antigen"; in-house preparation) together with TiterMax Gold (manufactured by TiterMax USA, Inc.). Two weeks later, the antigen together with a Freund's incomplete adjuvant (manufactured by Merck KGaA) was boosted to the mouse. Three days later, blood was collected from the tail vein, and increased in a blood antibody titer specific for ADAMTS13 MD was confirmed by ELISA based on a conventional method. Popliteal lymph nodes were recovered from the mouse with an increased antibody titer.

A single cell suspension was prepared from the popliteal lymph nodes in accordance with a method known in the art, which was fused with a 2-amino-6-mercaptopurine (6-thioguanine)-resistant mouse-derived cultured myeloma cell line (P3U1 cells) as a parent cell line in accordance with a method generally used in the art.

Then, the obtained fused cells were cultured in a culture medium supplemented with a HAT selection solution, to conduct cloning. Two or three weeks later, clones that produced the anti-ADAMTS13 MD monoclonal antibody of interest were screened by ELISA using a microplate adsorbed the ADAMTS13 MD antigen on a solid phase.

(2) Screening

A culture supernatant of the hybridoma cells was used in reaction with an ADAMTS13 MD antigen-immobilized ELISA plate to screen the antibody of interest. In this screening, clones that specifically reacted only with the ADAMTS13 MD antigen were selected by removing non-specific reactive clones that reacted with a nonspecific protein-immobilized ELISA plate. As a result, 1G2 antibody, 12D10 antibody, and 9A7 antibody were obtained.

Example 3: Human Chimerization of A10 Antibody

In this Example, the human chimerization of the antibody obtained in Example 1 was performed. Specifically, the heavy chain constant region (CH) and the light chain constant region (CL) of the antibody obtained in Example 1 was replaced with the heavy chain constant region (CH) and the light chain constant region (CL) of human IgG to perform the human chimerization.

(1) Acquisition of A10 Antibody Heavy Chain Gene and Light Chain Gene

A gene encoding the A10 antibody heavy chain and a gene encoding the A10 antibody light chain (heavy chain IgG2b gene and light chain Igk gene) were cloned from the cells that produced the A10 antibody obtained in Example 1. Specifically, total RNA extracted from the A10 antibody-producing cells was used as a template to perform reverse transcription reaction using SMART CDNA Library Construction Kit (Takara Bio Inc.) capable of amplifying 5' full-length cDNA in accordance with the attached protocol, to prepare cDNA.

The cDNA synthesized by the method described above was used as a template with KOD FX (TOYOBO Co., Ltd.) to preform PCR twice (1st PCR and 2nd PCR). In the 1st PCR, 1 μl (microlitter) of cDNA obtained by reverse transcription from each lymphoblastoid cell line (LCL) was used as a template with the following forward primer (Primer 1) and reverse primer (Primer 2) as primers to perform PCR reaction (reaction conditions: 94° C. for 2 min=>35 cycles of [98° C. for 10 sec, 55° C. for 30 sec, and 68° C. for 2 min]=>68° C. for 3 min).

TABLE 1

| Primer 1 | AAGCAGTGGTATCAACGCAGAGT | SEQ ID NO: 49 |
| Primer 2 | taggacctgagagctttgtgggt gctgagc | SEG ID NO: 50 |

In the 2nd PCR, 0.5 μl (microlitter) of the extension product of the 1st PCR was used as a template with the following forward primer (Primer 1) and reverse primer (Primer 2) as primers to perform PCR reaction (reaction conditions: 94° C. for 2 min=>35 cycles of [98° C. for 10 sec, 60° C. for 30 sec, and 68° C. for 2 min]=>68° C. for 3 min).

TABLE 2

| Primer 1 | ggggcggccgcAGAGTGGC CATTACGGCCGGG | SEQ ID NO: 51 |
| Primer 2 | GGGGAATTCtcatttaccc ggagaccgggagatgg | SEQ ID NO: 52 |

The PCR sample was applied to QIAquick Purification Kit (Qiagen N.V.) for the removal of unreacted primers and enzyme to obtain a purified PCR product.

The purified PCR product obtained by purification was treated with a restriction enzyme, was separated and purified by agarose gel electrophoresis, and then integrated in a vector. pQEFIP vector (retrovirus vector obtained by using pQCXIP (Takara Bio Inc.) as a backbone in which CMV promoter was replaced with human EF1 alpha promoter) was used for the preparation of a vector containing the heavy chain gene, and pQEFIN vector (retrovirus vector obtained by using pQCXIN (Takara Bio Inc.) as a backbone in which CMV promoter was replaced with human EF1 alpha promoter) was used for the preparation of a vector containing the light chain gene. The PCR product was integrated in the vectors using Ligation high (TOYOBO Co., Ltd.), which was used to transform competent cells (DH-5alpha; Nippon Gene Co., Ltd.).

Plasmid was extracted from the *E. coli* cultured in ampicillin-containing LB liquid medium using NucleoSpin Plasmid EasyPure (MACHEREY-NAGEL GmbH & Co. KG) in accordance with the attached protocol.

(2) Chimerization of Heavy Chain

A human IgG1 expression plasmid vector (in-house preparation) was used as a template with the following primers to perform PCR to amplify a fragment containing a human IgG1 constant region (using TOYOBO KOD plus neo) (reaction conditions: 94° C. for 2 min=>30 cycles of [98° C. for 10 sec, 58° C. for 30 sec, and 68° C. for 4.5 min]=>68° C. for 5 min).

TABLE 3

| Primer 1 | gcctccaccaagggcccatc | SEQ ID NO: 53 |
| Primer 2 | GCggccgcggtcaccAATTC | SEQ ID NO: 54 |

The A10 antibody IgG2b heavy chain expression plasmid vector was used as a template with the following primers to perform PCR to amplify a fragment containing the variable region of the A10 antibody heavy chain (IgG2b) (using TOYOBO KOD plus neo) (reaction conditions: 94° C. for 2 min=>30 cycles of [98° C. for 10 sec, 58° C. for 30 sec, and 68° C. for 30 sec]=>68° C. for 3 min).

TABLE 4

| Primer 1 | GAATTggtgaccgcggccGC AGAGTGGCCATTACGG | SEQ ID NO: 55 |
| Primer 2 | gggcccttggtggaggcTGC AGAGACAGTGACCAGA | SEQ ID NO: 56 |

Two PCR products (human IgG1 constant region and A10 antibody (IgG2b) variable region) obtained by the steps mentioned above were each treated with a restriction enzyme Dpn I (New England Biolabs Inc. (NEB)) at 37° C. for 30 minutes and were separated by agarose gel electrophoresis, followed by DNA extraction from the gel.

Two DNA fragments obtained were mixed and treated with NEBuilder HiFi DNA Assembly Master Mix (New England Biolabs Inc. (NEB)) at 50° C. for 15 minutes so that the fragments were bound with each other. This bound DNA was transformed to *E. coli* in accordance with a routine method, and a single colony was obtained to produce an A10 chimeric antibody (A10c antibody) heavy chain expression plasmid vector.

(3) Chimerization of Light Chain

The human Igk expression plasmid vector (in-house preparation) was used as a template with the following primers to perform PCR to amplify a fragment containing a human Igk constant region (using TOYOBO KOD plus neo).

TABLE 5

| Primer 1 | CGAACTGTGGCTGCACCATC | SEQ ID NO: 57 |
| Primer 2 | GCggccgcggtcaccAATTC | SEQ ID NO: 58 |

A fragment containing the variable region of the A10 antibody light chain (Igk) was amplified by PCR with the A10 antibody Igk expression plasmid vector as a template using the following primers (using TOYOBO KOD plus neo).

TABLE 6

| Primer 1 | GAATTggtgaccgcggccGCA GAGTGGCCATTACGG | SEQ ID NO: 59 |
| Primer 2 | gatggtgcagccacagttcgT TTCAGCTCCAGCTTGGTCCC | SEQ ID NO: 60 |

Two PCR products (human Igk constant region and A10 antibody Igk variable region) obtained by the steps mentioned above were each treated with a restriction enzyme Dpn I (New England Biolabs Inc. (NEB)) at 37° C. for 30 minutes and were separated by agarose gel electrophoresis, followed by DNA extraction from the gel.

Two DNA fragments obtained were mixed and treated with NEBuilder HiFi DNA Assembly Master Mix (New England Biolabs Inc. (NEB)) at 50° C. for 15 minutes so that the fragments were bound with each other. This bound DNA was transformed to *E. coli* in accordance with a routine method, and a single colony was obtained to produce an A10 chimeric antibody (A10c antibody) light chain expression plasmid vector.

(4) Expression of A10 Chimeric Antibody (A10c Antibody)

The A10 chimeric antibody (A10c antibody) heavy chain expression plasmid vector produced in the section (1) of this Example and the A10 chimeric antibody (A10c antibody) light chain expression plasmid vector produced in the section (2) of this Example were transiently cotransfected to Expi 293F cells (Thermo Fisher Scientific Inc.) using Expi293 Expression System (Thermo Fisher Scientific Inc.) to perform the expression and secretion of a recombinant antibody.

80 μL (microlitter) of ExpiFectamine 293 reagent and the plasmids (15 μg (microgram) each) of the heavy chain and the light chain were each mixed with 1.5 mL of Opti-MEM I (Gibco) and left standing at room temperature for 5 minutes. Then these two solutions were combined, left standing at room temperature for 20 minutes, and added to 4.5 to 5.5×10⁶ cells/mL (30 mL) of cells cultured in a 125 mL flask (Corning Inc.), followed by gyratory culture (37° C., 8% $CO_2$). After culture for 18 to 20 hours, 150 ML (microlitter) of ExpiFectamine 293 Transfection Enhancer 1 and 1.5 mL of ExpiFectamine 293 Transfection Enhancer 2 were added thereto, followed by gyratory culture for 5 to 6 days.

A recombinant antibody expressed by an expression system using the Expi 293F cells was purified using Protein G affinity chromatography (GE Hitrap protein GHP (1 mL)).

In this Example, A10c antibody was produced as a chimeric antibody based on the A10 antibody obtained in Example 1.

Example 4: Humanization of Antibody

In this Example, the antibody obtained in Example 1 was humanized.

DNA sequences encoding the amino acid sequence of the heavy chain (hereinafter, referred to as the H chain) (SEQ ID NO: 37) and the amino acid sequence of the κ light chain (hereinafter, referred to as the κL chain) (SEQ ID NO: 38) of the anti-mouse ADAMTS13 antibody clone A10 (hereinafter, referred to as the mouse A10 antibody) were analyzed by alignment to a mouse antibody germline gene sequences registered in a database to identify framework regions (FRs) (four FRs, i.e., FR1 to FR4), complementarity determining regions (CDRs) (three CDRs, i.e., CDR1 to CDR3), and somatic mutation sites in the H chain and the κL chain of the mouse A10 antibody. In the H chain, CDR1 to CDR3 of the mouse A10 antibody are shown in SEQ ID NOs: 1 to 3, and the framework regions FR1 to FR4 are moieties other than CDR1 to CDR3 in the heavy chain variable region (SEQ ID NO: 25). In the κL chain, CDR1 to CDR3 are shown in SEQ ID NOs: 4 to 6, and the framework regions FR1 to FR4 are moieties other than CDR1 to CDR3 in the light chain variable region (SEQ ID NO: 26).

Subsequently, the amino acid sequences of the H chain and the κL chain of the mouse A10 antibody (SEQ ID NO: 37 and SEQ ID NO: 38, respectively) were compared with the amino acid sequences of the H chain and the κL chain of each of human tetanus antibody clone 8A7 and clone 16E8 known in the art (hereinafter, referred to as human 8A7 antibody and human 16E8 antibody, respectively) [Japanese Patent Application No. 2020-089756] to identify a site where amino acid residues were different between the mouse A10 antibody and the human antibody (human 8A7 antibody and human 16E8 antibody).

On the basis of this comparative analysis, DNA fragments were designed such that the respective CDR1 to CDR3 moieties derived from the H chain and the κL chain of the mouse A10 antibody, and amino acids at somatic mutation locations among their neighboring amino acid residues were grafted to the H chain and the κL chain of the human antibody known in the art (human 8A7 antibody and human 16E8 antibody) by use of the CDR grafting method generally known as a humanized antibody preparation technique.

A leader sequence containing a Kozak sequence (ACCATGG) was added to each of the H chain and the κL chain of the humanized A10 antibody (humanized A10h/8A7 antibody and humanized A10h/16E8 antibody). Then, a codon optimization tool (https://www.vectorbuilder.jp/tool/codon-optimization.html) was used to optimize the frequency of codon usage of the leader sequence and the variable region (FR1-CDR1-FR2-CDR2-FR3-CDR3-FR4) of the humanized antibody in order to optimize antibody molecule expression in a human cultured cell line.

The DNA sequence of the humanized A10 antibody (A10h/8A7 antibody and A10h/16E8 antibody) having been optimized in frequency of codon usage was used to optimize the frequency of codon usage such that CAI (codon adaptation index; which is a non-dimensional number that varies in the range of 0 to 1, and means that a higher numeric value represents more optimal frequency of codon usage), an index for codon optimization, was 0.9 to 1.0.

DNA sequences encoding the heavy chain (H chain) and the light chain (κL chain) of the obtained humanized A10 antibody were ligated with separate expression plasmids by the method described in Example 3 to produce a heavy chain expression plasmid vector and a light chain expression plasmid vector of the humanized A10 antibody (A10h antibody).

The humanized A10 antibody (A10h/8A7 antibody and A10h/16E8 antibody) heavy chain expression plasmid vector and the humanized A10 antibody (A10h/8A7 antibody and A10h/16E8 antibody) light chain expression plasmid vector produced in this Example were transiently cotransfected to Expi 293F cells (Thermo Fisher Scientific Inc.) using Expi293 Expression System (Thermo Fisher Scientific Inc.) to perform the expression and secretion of a recombinant antibody.

80 μL (microlitter) of ExpiFectamine 293 reagent and the plasmids (15 μg (microgram) each) of the heavy chain and the light chain were each mixed with 1.5 mL of Opti-MEM I (Gibco) and left standing at room temperature for 5 minutes. Then these two solutions were combined, left standing at room temperature for 20 minutes, and added to 4.5 to 5.5×10⁶ cells/mL (30 mL) of cells cultured in a 125 mL flask (Corning Inc.), followed by gyratory culture (37° C., 8% $CO_2$). After culture for 18 to 20 hours, 150 μL (microlitter) of ExpiFectamine 293 Transfection Enhancer 1 and 1.5 mL of ExpiFectamine 293 Transfection Enhancer 2 were added thereto, followed by gyratory culture for 5 to 6 days.

A recombinant antibody expressed by an expression system using the Expi 293F cells was purified using Protein G affinity chromatography (GE Hitrap protein GHP (1 mL)).

In this Example, A10h/8A7 antibody (8A7 antibody-derived) and A10h/16E8 antibody (16E8 antibody-derived) were produced as two types of humanized antibodies as to the A10 antibody produced in Example 1.

Example 5: Amino acid sequence analysis of antibody

In this Example, the antibody prepared in Example 1, human chimerized antibody of Example 2, and humanized antibodies of Example 3 were analyzed for their amino acid sequences.
(A) Amino Acid Sequence Analysis of Derivative of A10 Antibody (A10c Antibody and A10h/8A7 Antibody)

In the amino acid sequence analysis on the A10c antibody, the A10 chimeric antibody (A10c antibody) heavy chain expression plasmid vector and the A10 chimeric antibody (A10c antibody) light chain expression plasmid vector produced in Example 3 were analyzed for their nucleotide sequences, and the amino acid sequence of the heavy chain and the amino acid sequence of the light chain were identified on the basis of the respective DNA sequences.

In the amino acid sequence analysis on the A10h/8A7 antibody and the A10h/16E8 antibody, the A10 humanized antibody (A10h/8A7 antibody and A10h/16E8 antibody) heavy chain expression plasmid vector and the A10 humanized antibody (A10h/8A7 antibody and A10h/16E8 antibody) light chain expression plasmid vector produced in Example 4 were analyzed for their nucleotide sequences, and the amino acid sequence of the heavy chain and the amino acid sequence of the light chain were identified on the basis of the respective DNA sequences.
(B) Amino Acid Sequence Analysis of 1G2 Antibody, 12D10 Antibody, and 9A7 Antibody In the amino acid sequence analysis on the 1G2 antibody, the 12D10 antibody, and the 9A7 antibody produced in Example 2, total RNA extracted from the antibody-producing cells was used as a template with SMART CDNA Library Construction Kit (Takara Bio Inc.) capable of amplifying 5' full-length cDNA in accordance with the attached protocol to prepare cDNA through reverse transcription reaction, in order to isolate heavy chain IgG1 gene or IgG2b gene and light chain Igk gene of the antibody gene (heavy chain IgG1 gene and light chain Igk gene for the 1G2 antibody; heavy chain IgG1 gene and light chain Igk gene for the 12D10 antibody; and heavy chain IgG2b gene and light chain Igk gene for the 9A7 antibody) from the cells that produced the 1G2 antibody, the 12D10 antibody, or the 9A7 antibody.

The cDNA synthesized by the method described above wase used as a template with KOD FX (TOYOBO Co., Ltd.) to preform PCR twice (1st PCR and 2nd PCR). In the 1st PCR, 1 μl (microlitter) of cDNA obtained by reverse transcription from each lymphoblastoid cell line (LCL) was used as a template with the following forward primer (Primer 1) and reverse primer (Primer 2) as primers to perform PCR reaction (reaction conditions: 94° C. for 2 min=>35 cycles of [98° C. for 10 sec, 55° C. for 30 sec, and 68° C. for 2 min]=>68° C. for 3 min).

TABLE 7

| Primer 1 | AAGCAGTGGTATCAACGCAGAGT | SEQ ID NO: 61 |
|---|---|---|
| Primer 2 | | |
| 1G2, 12D10 | taggaccagagggctccaaggac actggga | SEQ ID NO: 62 |
| 9A7 | taggacctgagagctttgtgggt gctgagc | SEQ ID NO: 50 |

In the 2nd PCR, 0.5 μl (microlitter) of the extension product of the 1st PCR was used as a template with the following forward primer (Primer 1) and reverse primer (Primer 2) as primers to perform PCR reaction (reaction conditions: 94° C. for 2 min=>35 cycles of [98° C. for 10 sec, 60° C. for 30 sec, and 68° C. for 2 min]=>68° C. for 3 min).

TABLE 8

| Primer 1 | ggggcggccgcAGAGTGGCCA TTACGGCCGGG | SEQ ID NO: 63 |
|---|---|---|
| Primer 2 | | |
| 1G2, 12D10 | GGGGAATTCtcatttaccagg agagtgggagaggc | SEQ ID NO: 64 |
| 9A7 | GGGGAATTCtcatttacccgg agaccgggagatgg | SEQ ID NO: 52 |

The PCR sample was applied to QIAquick Purification Kit (Qiagen N.V.) for the removal of unreacted primers and enzyme to obtain a purified PCR product.

The purified PCR product obtained by purification was treated with a restriction enzyme, was separated and purified by agarose gel electrophoresis, and then integrated in a vector. pQEFIP vector (retrovirus vector obtained by using pQCXIP (Takara Bio Inc.) as a backbone in which CMV promoter was replaced with human EF1 alpha promoter) was used for the preparation of a vector containing the heavy chain gene, and pQEFIN vector (retrovirus vector obtained by using pQCXIN (Takara Bio Inc.) as a backbone in which CMV promoter was replaced with human EF1 alpha promoter) was used for the preparation of a vector containing the light chain gene. The PCR product was integrated in the vectors using Ligation high (TOYOBO Co., Ltd.), which was used to transform competent cells (DH-5alpha; Nippon Gene Co., Ltd.).

Plasmid was extracted from the *E. coli* cultured in ampicillin-containing LB liquid medium using NucleoSpin Plasmid EasyPure (MACHEREY-NAGEL GmbH & Co. KG) in accordance with the attached protocol.

The heavy chain expression plasmid vectors and the light chain expression plasmid vectors for these antibodies were analyzed for their nucleotide sequences, and the amino acid sequences of the heavy chain and the amino acid sequences of the light chain of these antibodies were identified on the basis of the respective DNA sequences.

The results of amino acid sequence analysis were as follows.

(1-1) A10c Antibody (Chimeric A10 Antibody)
(1-1-1) Heavy Chain
Full-length amino acid sequence of the heavy chain: SEQ ID NO: 37
Amino acid sequence of the heavy chain variable region VH domain: SEQ ID NO: 25
As a result of analyzing complementarity determining regions (CDR1, CDR2, and CDR3) in this sequence, the following was confirmed:
Heavy chain complementarity determining regions: CDR1 (GYSFTGYT, SEQ ID NO: 1), CDR2 (INPYNGGT, SEQ ID NO: 2), and CDR3 (ARTSGYLFAY, SEQ ID NO: 3).
(1-1-2) Light chain
Full-length amino acid sequence of the light chain: SEQ ID NO: 38
Amino acid sequence of the light chain variable region VL domain: SEQ ID NO: 26
As a result of analyzing complementarity determining regions (CDR1, CDR2, and CDR3) in this sequence, the following was confirmed:
Light chain complementarity determining regions: CDR1 (EDIYNR, SEQ ID NO: 4), CDR2 (GAT, SEQ ID NO: 5), and CDR3 (QQYWSSPLT, SEQ ID NO: 6).
(1-2) A10h/8A7 Antibody (Humanized A10 Antibody)
(1-2-1) Heavy Chain
Full-length amino acid sequence of the heavy chain: SEQ ID NO: 39
Amino acid sequence of the heavy chain variable region VH domain: SEQ ID NO: 27
As a result of analyzing complementarity determining regions (CDR1, CDR2, and CDR3) in this sequence, the following was confirmed:
Heavy chain complementarity determining regions: CDR1 (GYSFTGYT, SEQ ID NO: 1), CDR2 (INPYNGGT, SEQ ID NO: 2), and CDR3 (ARTSGYLFAY, SEQ ID NO: 3).
(1-2-2) Light Chain
Full-length amino acid sequence of the light chain: SEQ ID NO: 40
Amino acid sequence of the light chain variable region VL domain: SEQ ID NO: 28

As a result of analyzing complementarity determining regions (CDR1, CDR2, and CDR3) in this sequence, the following was confirmed:
Light chain complementarity determining regions: CDR1 (EDIYNR, SEQ ID NO: 4), CDR2 (GAT, SEQ ID NO: 5), and CDR3 (QQYWSSPLT, SEQ ID NO: 6).
(1-3) A10h/16E8 Antibody (Humanized A10 Antibody)
(1-3-1) Heavy Chain
Full-length amino acid sequence of the heavy chain: SEQ ID NO: 41
Amino acid sequence of the heavy chain variable region VH domain: SEQ ID NO: 29
As a result of analyzing complementarity determining regions (CDR1, CDR2, and CDR3) in this sequence, the following was confirmed:
Heavy chain complementarity determining regions: CDR1 (GYSFTGYT, SEQ ID NO: 1), CDR2 (INPYNGGT, SEQ ID NO: 2), and CDR3 (ARTSGYLFAY, SEQ ID NO: 3).
(1-3-2) Light Chain
Full-length amino acid sequence of the light chain: SEQ ID NO: 42
Amino acid sequence of the light chain variable region VL domain: SEQ ID NO: 30
As a result of analyzing complementarity determining regions (CDR1, CDR2, and CDR3) in this sequence, the following was confirmed:
Light chain complementarity determining regions: CDR1 (EDIYNR, SEQ ID NO: 4), CDR2 (GAT, SEQ ID NO: 5), and CDR3 (QQYWSSPLT, SEQ ID NO: 6).
(2) 1G2 Antibody
(2-1) Heavy Chain
Full-length amino acid sequence of the heavy chain: SEQ ID NO: 43
Amino acid sequence of the heavy chain variable region VH domain: SEQ ID NO: 31
As a result of analyzing complementarity determining regions (CDR1, CDR2, and CDR3) in this sequence, the following was confirmed:
Heavy chain complementarity determining regions: CDR1 (GFSLPRYG, SEQ ID NO: 7), CDR2 (IWAGGST, SEQ ID NO: 8), and CDR3 (ARAGGSOPFDY, SEQ ID NO: 9).
(2-2) Light Chain
Full-length amino acid sequence of the light chain: SEQ ID NO: 44
Amino acid sequence of the light chain variable region VL domain: SEQ ID NO: 32
As a result of analyzing complementarity determining regions (CDR1, CDR2, and CDR3) in this sequence, the following was confirmed:
Light chain complementarity determining regions: CDR1 (RDINTY, SEQ ID NO: 10), CDR2 (RAN, SEQ ID NO: 11), and CDR3 (LOYDEFPWT, SEQ ID NO: 12).
(3) 12D10 Antibody
(3-1) Heavy Chain
Full-length amino acid sequence of the heavy chain: SEQ ID NO: 45
Amino acid sequence of the heavy chain variable region VH domain: SEQ ID NO: 33
As a result of analyzing complementarity determining regions (CDR1, CDR2, and CDR3) in this sequence, the following was confirmed:
Heavy chain complementarity determining regions: CDR1 (GFSLTRYG, SEQ ID NO: 13), CDR2 (IWAGGST, SEQ ID NO: 14), and CDR3 (ARAGGSSSFDY, SEQ ID NO: 15).

(3-2) Light Chain

Full-length amino acid sequence of the light chain: SEQ ID NO: 46

Amino acid sequence of the light chain variable region VL domain: SEQ ID NO: 34

As a result of analyzing complementarity determining regions (CDR1, CDR2, and CDR3) in this sequence, the following was confirmed:

Light chain complementarity determining regions: CDR1 (QDINTY, SEQ ID NO: 16), CDR2 (RAN, SEQ ID NO: 17), and CDR3 (LOYDEFPWT, SEQ ID NO: 18).

(4) 9A7 Antibody (4-1) Heavy Chain

Full-length amino acid sequence of the heavy chain: SEQ ID NO: 47

Amino acid sequence of the heavy chain variable region VH domain: SEQ ID NO: 35

As a result of analyzing complementarity determining regions (CDR1, CDR2, and CDR3) in this sequence, the following was confirmed:

Heavy chain complementarity determining regions: CDR1 (GFSLTGYG, SEQ ID NO: 19), CDR2 (IWADGTT, SEQ ID NO: 20), and CDR3 (ARAGGSOPFDY, SEQ ID NO: 21).

(4-2) Light chain

Full-length amino acid sequence of the light chain: SEQ ID NO: 48

Amino acid sequence of the light chain variable region VL domain: SEQ ID NO: 36

As a result of analyzing complementarity determining regions (CDR1, CDR2, and CDR3) in this sequence, the following was confirmed:

Light chain complementarity determining regions: CDR1 (QDINSY, SEQ ID NO: 22), CDR2 (RAN, SEQ ID NO: 23), and CDR3 (LOYDEFPWT, SEQ ID NO: 24).

Example 6: In Vitro Binding Property Analysis of Antibodies

In this Example, a binding property to the target molecule ADAMTS13 among chimeric antibodies of various types using the heavy chain and the light chain of each antibody prepared in Example 1 and Example 2 and the heavy chain and the light chain of each human chimerized antibody prepared in Example 3 were compared and studied for change in a binding property by chimerization of various types of antibodies.

The antibodies used in this Example were recombinant A10 antibody consisting of the heavy chain or the light chain of the mouse A10 antibody, and recombinant human chimeric antibody (A10c antibody) consisting of the heavy chain or the light chain of the A10c antibody prepared in Example 3.

A antibody for detection for use in detecting each antibody (A10c antibody and A10 antibody) was an anti-human IgG antibody for the A10c antibody and an anti-mouse IgG antibody for the A10 antibody which were each used as a "secondary antibody".

Figure 3:
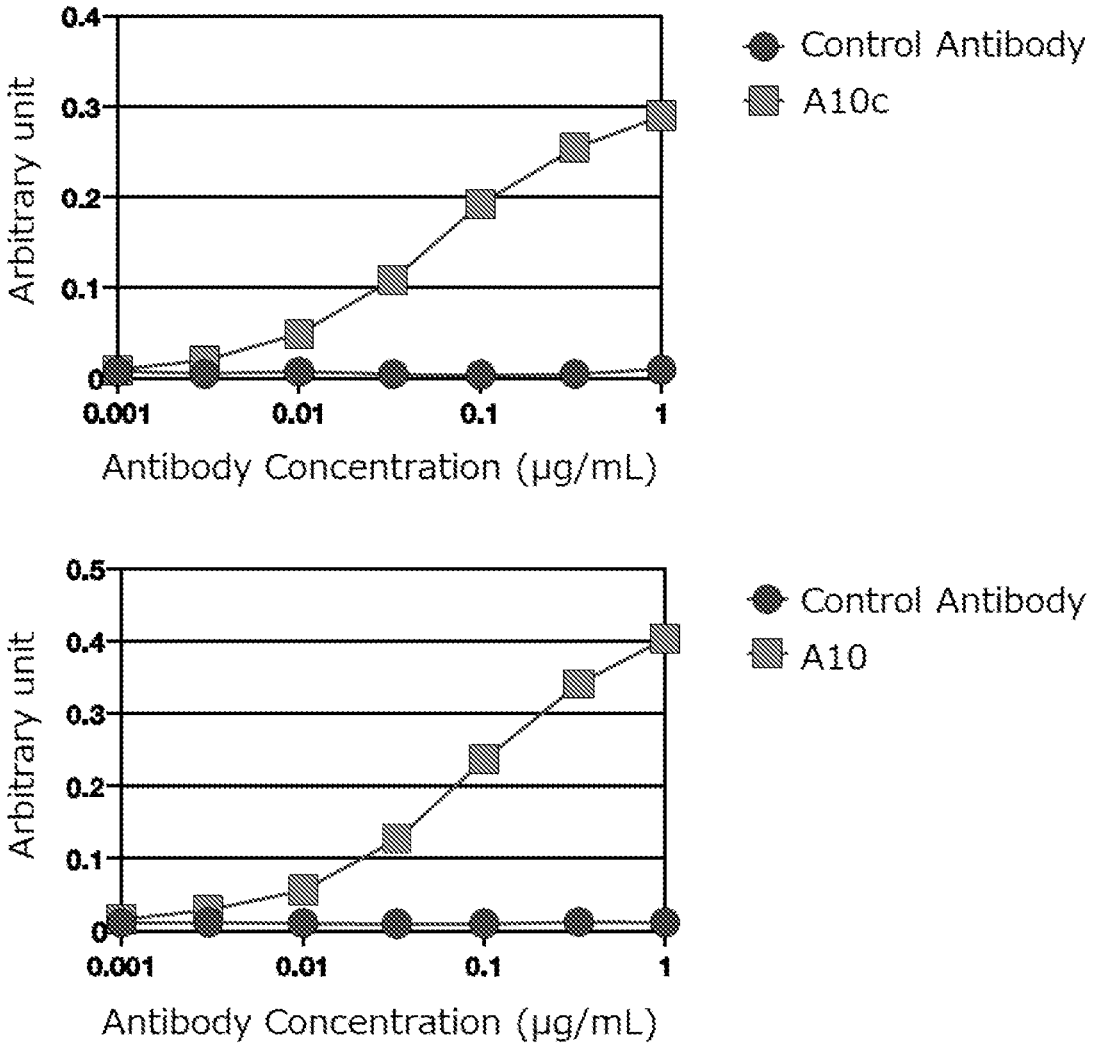
FIG. 3 is a figure showing the ADAMTS13 binding activity of anti-ADAMTS13 antibodies (mouse A10 antibody and human chimeric A10c antibody).

The binding property was measured by ELISA using wells on which 50 ng of the ADAMTS13 MD recombinant antigen (in-house preparation) was immobilized. Specifically, ADAMTS13 MD was diluted into 1 μg (microgram)/mL with PBS, added at 50 μL (microlitter)/well to a 96-well plate for ELISA (NUNC), and left standing overnight at 4° C. The plate was washed three times (250 μL (microlitter)/well of PBS-T (0.1% Tween 20 in PBS)), and after addition of 250 μL (microlitter)/well of a blocking buffer (2% BSA, 0.05% NaN3 in PBS), left standing at room temperature for 1 hour. Then the 96-well plate was washed once (250 μL (microlitter)/well of PBS-T). Each recombinant antibody (A10c antibody and A10 antibody) was concentration-adjusted and then 50 μL (microlitter)/well of recombinant antibody was added to each well of the plate, which was left standing at room temperature for 2 hours. Each recombinant antibody was used at concentrations of $1\times10^-$μg (microgram)/mL, $5\times10^{-3}$ μg (microgram)/mL, $1\times10$–2 μg (microgram)/mL, $5\times10^{-2}$ μg (microgram)/mL, $1\times10^{-1}$ μg (microgram)/mL, $5\times10^{-1}$ μg (microgram)/mL, and 1 μg (microgram)/mL, as also shown in FIG. 3.

Then the 96-well plate was washed three times (250 μL (microlitter)/well of PBS-T). An alkaline phosphatase-labeled secondary antibody (goat anti-human IgG-AP and goat anti-mouse IgG-AP (SouthernBiotech)) was diluted 1/1000-fold with PBS-T and added at 50 ML (microlitter)/well, and the plate was left standing at room temperature for 1 hour. Then the 96-well plate was washed once (250 μL (microlitter)/well of PBS-T). Then, a chromogenic substrate solution containing one particle of a phosphatase substrate (Sigma) dissolved in 25 mL of 0.1 M glycine buffer was added at 100 μL (microlitter)/well. Absorbance at 405 nm and 650 nm was measured using multimode reader EnSpire (PerkinElmer Enspire).

As a result, both the tested antibodies (A10c antibody and A10 antibody) bound to ADAMTS13. The binding strength of the engineered antibodies to ADAMTS13 was not altered by chimerization (in A10c antibody), and dose-dependent reactivity with the antigen was shown, as in the A10 antibody (see, FIG. 3).

Example 7: In Vitro Inhibitory Effect Analysis of Antibodies

In this Example, the A10 antibody prepared in Example 1 and the 1G2 antibody, the 12D10 antibody, and the 9A7 antibody prepared in Example 2 were analyzed for their inhibitory effects on the VWF cleaving activity of the target molecule ADAMTS13.

20 μL (microlitter) of 0.2 to 200 μg (microgram)/mL each antibody (A10 antibody produced in Example 1 and 1G2 antibody, 12D10 antibody, and 9A7 antibody produced in Example 2) were mixed with 50 μL (microlitter) of normal human plasma to adjust a final concentration to 0.01 to 100 μg (microgram)/mL. Then, the mixture was incubated at 37° C. for 15 minutes, followed by the measurement of ADAMTS13 activity remaining in the human plasma by ELISA (KAINOS Laboratories, Inc.).

Figure 4:
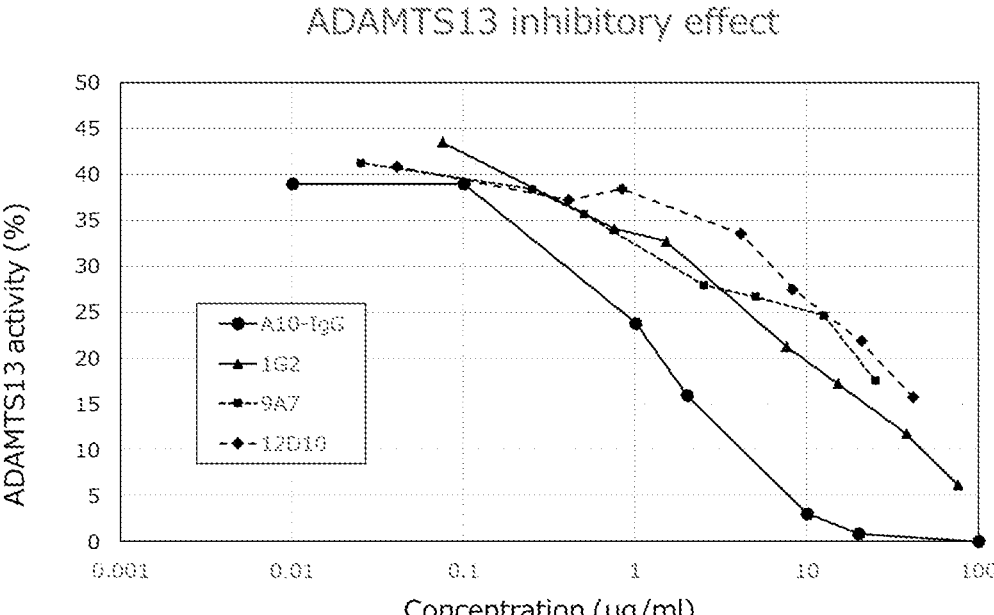
FIG. 4 is a figure showing an inhibitory effect of an anti-ADAMTS13 antibody on the ADAMTS13 activity (A10c antibody).

As a result, the A10 antibody exhibited an inhibitory effect with an ID50 concentration of approximately 1.55 μg (microgram)/mL on the VWF cleaving activity of ADAMTS13 and exhibited a complete (almost 100%) inhibitory effect at 50 μg (microgram)/mL or higher (see, FIG. 4).

The 1G2 antibody exhibited an inhibitory effect with an ID50 concentration of approximately 7.28 μg (microgram)/mL on the VWF cleaving activity of ADAMTS13, the 12D10 antibody exhibited an inhibitory effect with an ID50 concentration of approximately 25.4 μg (microgram)/mL on the VWF cleaving activity of ADAMTS13, and the 9A7 antibody exhibited an inhibitory effect with an ID50 concentration of approximately 19.5 μg (microgram)/mL on the VWF cleaving activity of ADAMTS13 (see, FIG. 4).

Example 8: In Vitro Functional Analysis of Humanized Antibody

In this Example, a binding property to and inhibitory activity against the target molecule ADAMTS13 were compared and studied for change by humanization in its function (binding property and inhibitory activity) of humanized antibody prepared in Example 4 (A10h/8A7 antibody and A10h/16E8 antibody) when compared with the human chimerized antibody of Example 3.

The binding property analysis was conducted in the same manner as in Example 6 except that a plurality of concentrations of the target molecule ADAMTS13 were set. The goat anti-human IgG-AP was used as a secondary antibody.

Figure 5:
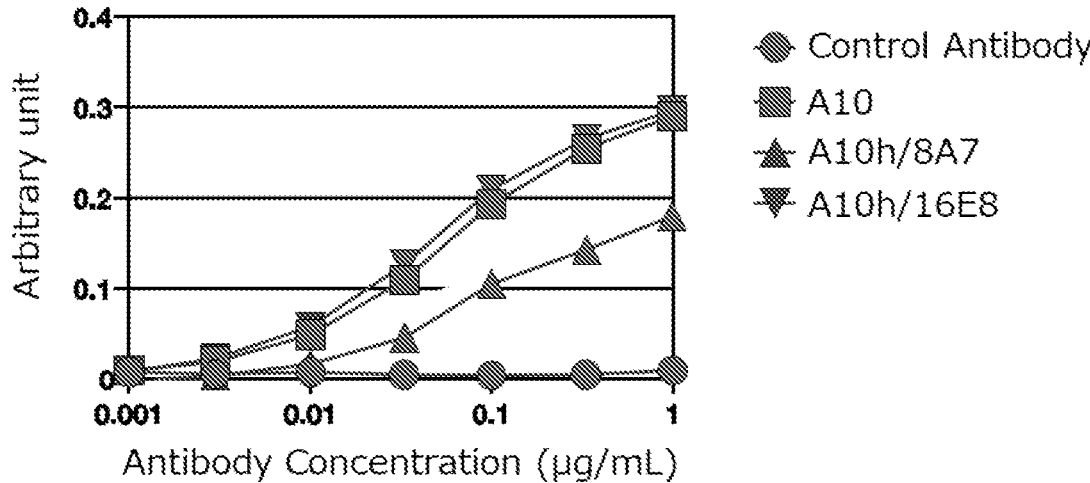
FIG. 5 is a figure showing concentration-binding correlation for the ADAMTS13 binding activity of anti-AD-AMTS13 antibodies (A10h/8A7 antibody and A10h/16E8 antibody).

As a result, the tested A10h/16E8 antibody (the humanized antibody of the A10 antibody) exhibited a binding property to ADAMTS13 at almost the same level as that of the A10c antibody (the human chimeric antibody of the A10 antibody) with its binding property confirmed in Example 6 (see, FIG. 5). On the other hand, the A10h/8A7 antibody (the humanized antibody of the A10 antibody) was found to maintain binding strength on the order of 60% of the binding strength of the A10c antibody (the human chimeric antibody of the A10 antibody), though the binding property to ADAMTS13 was reduced as compared with the A10c antibody (see, FIG. 5). These results demonstrated that the A10 antibody, even if humanized, exhibits dose-dependent reactivity with the ADAMTS13 antigen, as in the chimeric antibody (A10c antibody).

Subsequently, the inhibitory activity of each antibody (A10h/8A7 antibody, A10h/16E8 antibody, A10 antibody, and A10c antibody) was measured in the same manner as in Example 7.

Figure 6:
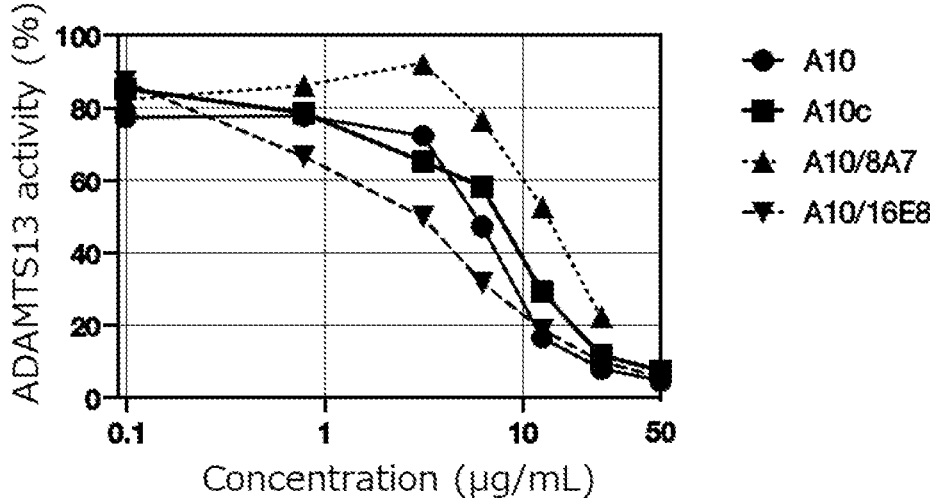
FIG. 6 is a figure showing the ADAMTS13 activity inhibitory effect of anti-ADAMTS13 antibodies (A10h/8A7 antibody and A10h/16E8 antibody).

As a result, the tested A10h/16E8 antibody (the humanized antibody of the A10 antibody) exhibited, in a dose-dependent manner, higher inhibitory activity against ADAMTS13 than that of the A10 antibody with its inhibitory activity confirmed in Example 7 (see, FIG. 6). On the other hand, the A10h/8A7 antibody (the humanized antibody of the A10 antibody) exhibited dose-dependent inhibitory activity against ADAMTS13, as in the A10h/16E8 antibody, though the inhibitory activity against ADAMTS13 was reduced as compared with the A10 antibody (see, FIG. 6). The A10 antibody and the A10c antibody (the human chimeric antibody of the A10 antibody) were found to have almost the same level of inhibitory activity (see, FIG. 6). These results demonstrated that the A10 antibody, even if humanized, exhibits dose-dependent inhibitory activity against the ADAMTS13 antigen, as in the chimeric antibody (A10c antibody).

In this Example, the ID50 value of each antibody against the VWF cleaving activity of ADAMTS13 was calculated. As a result, each antibody was found to have the following ID50 value (see, FIG. 6):

A10 antibody=5.97 µg (microgram)/mL;
A10c antibody=6.92 µg (microgram)/mL;
A10h/8A7 antibody=13.04 µg (microgram)/mL; and
A10h/16E8 antibody=2.52 µg (microgram)/mL.

Example 9: In Vitro Inhibitory Effect Analysis of Antibodies

In this Example, the cleavage of a VWF multimer that occurred in blood under high shear stress applied to the blood was varidated to confirm how the antibodies against ADAMTS13 of the present invention had an effect on the cleavage of a VWF multimer.

First, human plasma was loaded with high shear stress, and VWF cleavage by ADAMTS13 was confirmed by VWF multimer analysis. The high shear stress was loaded by placing plasma in two 1 mL syringes or two 2.5 mL syringes (both from TERUMO Corp.) connected through an 18-G injection needle (TERUMO Corp.), and moving the plasma between the syringes once every second for 6 minutes (360 times) so that the plasma passed through the injection needle (see, J Thromb Haemost, 2019; 17:975-983). In this operation, high shear stress of 108 dyne/cm$^2$, 216 dyne/cm$^2$, and 324 dyne/cm$^2$ were generated at plasma volumes of 440 µL (microliter), 880 µL (microliter), and 1320 µL (microliter), respectively. The high shear stress of 324 dyne/cm$^2$ is very high shear stress that is not observed in the body of a healthy person.

In the VWF multimer analysis, the plasma was electrophoresed on SDS-1.0% agarose gel and visualized by Western blot. The antibody for detection used was VWF polyclonal antibody (Dako).

Figure 7:
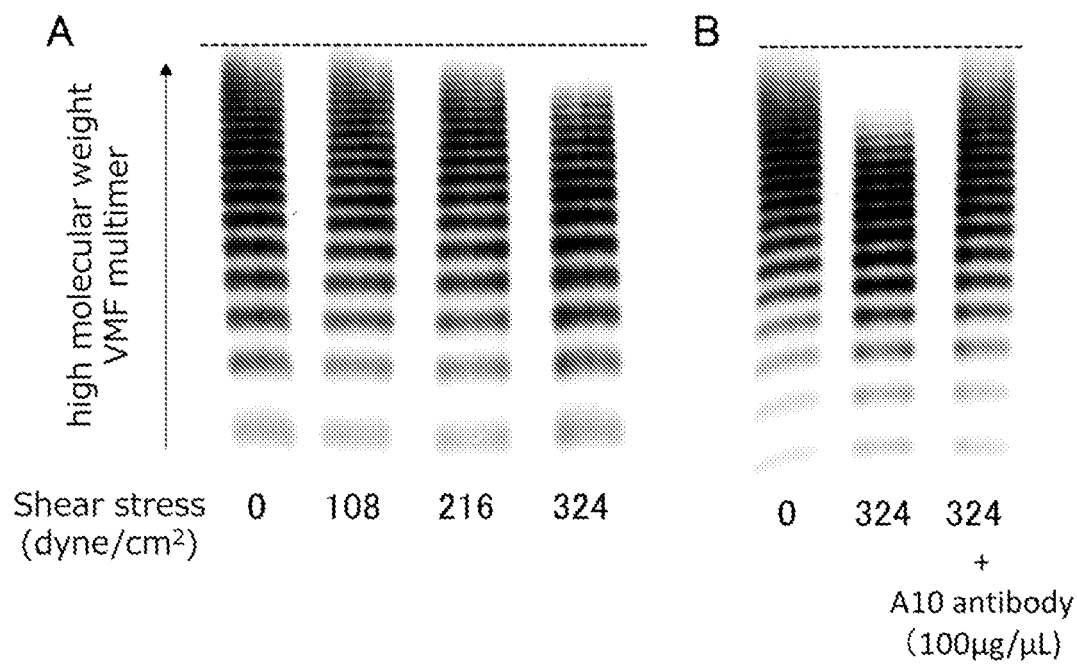
FIG. 7 is a figure showing change in high molecular weight VWF multimer deficiency by shear stress (FIG. 7A) and the inhibition of high molecular weight VWF multimer deficiency by the addition of A10 antibody (FIG. 7B).

As a result, more deficiency in high-molecular-weight VWF multimer and stronger cleavage of VWF were shown with increase in shear stress of 108 dyne/cm$^2$, 216 dyne/cm$^2$, and 324 dyne/cm$^2$ (see, FIG. 7A).

Next, the A10 antibody prepared in Example 1 was added at 100 µg (microgram)/mL to the plasma. After 15 minutes, high shear stress of 324 dyne/cm$^2$ was generated in the same manner as above, and the cleavage of a VWF multimer was analyzed by the same method as above.

As a result, the absence of VWF cleavage by the addition of the anti-ADAMTS13 antibody was able to be observed even when loaded with high shear stress of 324 dyne/cm$^2$ (see, FIG. 7B). This suggested that the anti-ADAMTS13 antibody can prevent the development of AVWS caused by the excessive cleavage of VWF by ADAMTS13 under abnormally high shear stress.

INDUSTRIAL APPLICABILITY

The present invention can provide an antibody or an antibody derivative that has specific binding activity against ADAMTS13, VWF cleaving protease, which is considered as a causative factor of the acquired von Willebrand syndrome (AVWS) in humans, and can reduce the excessive cleavage of VWF by ADAMTS13. Since the excessive cleavage of VWF by ADAMTS13 is considered as pathogenesis of the human acquired von Willebrand syndrome (AVWS), the present invention can also provide a pharmaceutical composition for preventing or treating human AVWS, comprising the antibody or the antibody derivative of the present invention.

FREE TEXT OF SEQUENCE LISTING

Heavy chain complementarity determining regions of A10c antibody, A10h/8A7 antibody, and A10h/16E8 antibody: CDR1 (GYSFTGYT, SEQ ID NO: 1), CDR2 (INPYNGGT, SEQ ID NO: 2), and CDR3 (ARTSGYLFAY, SEQ ID NO: 3)
Light chain complementarity determining regions of A10c antibody, A10h/8A7 antibody, A10h/16E8 antibody: CDR1 (EDIYNR, SEQ ID NO: 4), CDR2 (GAT, SEQ ID NO: 5), and CDR3 (QQYWSSPLT, SEQ ID NO: 6) 1G2 antibody Heavy chain complementarity determining regions: CDR1 (GFSLPRYG, SEQ ID NO: 7), CDR2 (IWAGGST, SEQ ID NO: 8), and CDR3 (ARAGGSOPFDY, SEQ ID NO: 9)
1G2 antibody Light chain complementarity determining regions: CDR1 (RDINTY, SEQ ID NO: 10), CDR2 (RAN, SEQ ID NO: 11), and CDR3 (LOYDEFPWT, SEQ ID NO: 12)
12D10 antibody Heavy chain complementarity determining regions: CDR1 (GFSLTRYG, SEQ ID NO: 13), CDR2 (IWAGGST, SEQ ID NO: 14), and CDR3 (ARAGGSSSFDY, SEQ ID NO: 15)

12D10 antibody Light chain complementarity determining regions: CDR1 (QDINTY, SEQ ID NO: 16), CDR2 (RAN, SEQ ID NO: 17), and CDR3 (LOYDEFPWT, SEQ ID NO: 18)

9A7 antibody Heavy chain complementarity determining regions: CDR1 (GFSLTGYG, SEQ ID NO: 19), CDR2 (IWADGTT, SEQ ID NO: 20), and CDR3 (ARAGGSQPFDY, SEQ ID NO: 21)

9A7 antibody Light chain complementarity determining regions: CDR1 (QDINSY, SEQ ID NO: 22), CDR2 (RAN, SEQ ID NO: 23), and CDR3 (LOYDEFPWT, SEQ ID NO: 24)

Amino acid sequence of A10c antibody heavy chain variable region VH domain: SEQ ID NO: 25

Amino acid sequence of A10c antibody light chain variable region VL domain: SEQ ID NO: 26

Amino acid sequence of A10h/8A7 antibody heavy chain variable region VH domain: SEQ ID NO: 27

Amino acid sequence of A10h/8A7 antibody light chain variable region VL domain: SEQ ID NO: 28

Amino acid sequence of A10h/16E8 antibody heavy chain variable region VH domain: SEQ ID NO: 29

Amino acid sequence of A10h/16E8 antibody light chain variable region VL domain: SEQ ID NO: 30

Amino acid sequence of 1G2 antibody heavy chain variable region VH domain: SEQ ID NO: 31

Amino acid sequence of 1G2 antibody light chain variable region VL domain: SEQ ID NO: 32

Amino acid sequence of 12D10 antibody heavy chain variable region VH domain: SEQ ID NO: 33

Amino acid sequence of 12D10 antibody light chain variable region VL domain: SEQ ID NO: 34

Amino acid sequence of 9A7 antibody heavy chain variable region VH domain: SEQ ID NO: 35

Amino acid sequence of 9A7 antibody light chain variable region VL domain: SEQ ID NO: 36

Full-length amino acid sequence of A10c antibody heavy chain: SEQ ID NO: 37

Full-length amino acid sequence of A10c antibody light chain: SEQ ID NO: 38

Full-length amino acid sequence of A10h/8A7 antibody heavy chain: SEQ ID NO: 39

Full-length amino acid sequence of A10h/8A7 antibody light chain: SEQ ID NO: 40

Full-length amino acid sequence of A10h/16E8 antibody heavy chain: SEQ ID NO: 41

Full-length amino acid sequence of A10h/16E8 antibody light chain: SEQ ID NO: 42

Full-length amino acid sequence of 1G2 antibody heavy chain: SEQ ID NO: 43

Full-length amino acid sequence of 1G2 antibody light chain: SEQ ID NO: 44

Full-length amino acid sequence of 12D10 antibody heavy chain: SEQ ID NO: 45

Full-length amino acid sequence of 12D10 antibody light chain: SEQ ID NO: 46

Full-length amino acid sequence of 9A7 antibody heavy chain: SEQ ID NO: 47

Full-length amino acid sequence of 9A7 antibody light chain: SEQ ID NO: 48

Primer sequences used in Example 5: SEQ ID NO: 49 to SEQ ID NO: 64

The invention claimed is:

1. An antibody or an antibody derivative thereof capable of binding to ADAMTS13 and having an inhibitory effect on von Willebrand factor (VWF) cleaving activity, comprising heavy chain and light chain complementarity determining regions selected from the group consisting of:

(1) heavy chain complementarity determining regions CDR1 (GYSFTGYT, SEQ ID NO: 1), CDR2 (INPYN-GGT, SEQ ID NO: 2), and CDR3 (ARTSGYLFAY, SEQ ID NO: 3), and light chain complementarity determining regions CDR1 (EDIYNR, SEQ ID NO: 4), CDR2 (GAT), and CDR3 (QQYWSSPLT, SEQ ID NO: 6);

(2) heavy chain complementarity determining regions CDR1 (GFSLPRYG, SEQ ID NO: 7), CDR2 (IWAGGST, SEQ ID NO: 8), and CDR3 (ARAGGSQPFDY, SEQ ID NO: 9), and light chain complementarity determining regions CDR1 (RDINTY, SEQ ID NO: 10), CDR2 (RAN), and CDR3 (LQYDEFPWT, SEQ ID NO: 12);

(3) heavy chain complementarity determining regions CDR1 (GFSLTRYG, SEQ ID NO: 13), CDR2 (IWAGGST, SEQ ID NO: 14), and CDR3 (ARAGGSSSFDY, SEQ ID NO: 15), and light chain complementarity determining regions CDR1 (QDINTY, SEQ ID NO: 16), CDR2 (RAN), and CDR3 (LQYDEFPWT, SEQ ID NO: 18); and (4) heavy chain complementarity determining regions CDR1 (GFSLTGYG, SEQ ID NO: 19), CDR2 (IWADGTT, SEQ ID NO: 20), and CDR3 (ARAGGSQPFDY, SEQ ID NO: 21), and light chain complementarity determining regions CDR1 (QDINSY, SEQ ID NO: 22), CDR2 (RAN), and CDR3 (LQYDEFPWT, SEQ ID NO: 24).

2. The antibody or the antibody derivative according to claim 1, wherein the antibody or the antibody derivative is a recombinant type.

3. The antibody or the antibody derivative according to claim 1, wherein the antibody derivative is selected from the group consisting of an engineered antibody, a humanized antibody, a chimeric antibody, a single-chain antibody, a multivalent antibody, a multispecific antibody, and a functional fragment thereof.

4. The antibody or the antibody derivative according to claim 1, wherein an amino acid sequence of a heavy chain variable region VH domain of the antibody or the antibody derivative is selected from the group consisting of:

(1-1) the amino acid sequence of SEQ ID NO: 25, or an amino acid sequence having a substitution, insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 25, (1-2) the amino acid sequence of SEQ ID NO: 27, or an amino acid sequence having a substitution, insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 27, (1-3) the amino acid sequence of SEQ ID NO: 29, or an amino acid sequence having a substitution, insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 29, (2) the amino acid sequence of SEQ ID NO: 31, or an amino acid sequence having a substitution, insertion, or deletion of one or several amino acids at a moiety except for CDR1 (SEQ ID NO: 7), CDR2 (SEQ ID NO: 8), and CDR3 (SEQ ID NO: 9) in the amino acid sequence of SEQ ID NO: 31, (3) the amino acid sequence of SEQ ID NO: 33, or an amino acid sequence having a substitution, insertion, or deletion of one or several amino acids at a moiety except for CDR1 (SEQ ID NO: 13), CDR2 (SEQ ID NO: 14), and CDR3 (SEQ ID NO: 15) in the amino acid sequence of SEQ ID NO: 33, and (4) the amino acid sequence of SEQ ID NO: 35, or an amino acid sequence having a substitution, insertion, or deletion of one or several amino acids at a moiety except for CDR1 (SEQ ID NO: 19), CDR2 (SEQ ID NO: 20), and CDR3 (SEQ ID NO: 21) in the amino acid sequence of SEQ ID NO: 35.

5. The antibody or the antibody derivative according to claim 1, wherein an amino acid sequence of a light chain variable region VL domain of the antibody or the antibody derivative is selected from the group consisting of:

(1-1) the amino acid sequence of SEQ ID NO: 26, or an amino acid sequence having a substitution, insertion, or deletion of one or several amino acids at a moiety except for CDR1 (SEQ ID NO: 4), CDR2 (GAT), and CDR3 (SEQ ID NO: 6) in the amino acid sequence of SEQ ID NO: 26, (1-2) the amino acid sequence of SEQ ID NO: 28, or an amino acid sequence having a substitution, insertion, or deletion of one or several amino acids at a moiety except for CDR1 (SEQ ID NO: 4), CDR2 (GAT), and CDR3 (SEQ ID NO: 6) in the amino acid sequence of SEQ ID NO: 28, (1-3) the amino acid sequence of SEQ ID NO: 30, or an amino acid sequence having a substitution, insertion, or deletion of one or several amino acids at a moiety except for CDR1 (SEQ ID NO: 4), CDR2 (GAT), and CDR3 (SEQ ID NO: 6) in the amino acid sequence of SEQ ID NO: 30, (2) the amino acid sequence of SEQ ID NO: 32, or an amino acid sequence having a substitution, insertion, or deletion of one or several amino acids at a moiety except for CDR1 (SEQ ID NO: 10), CDR2 (RAN), and CDR3 (SEQ ID NO: 12) in the amino acid sequence of SEQ ID NO: 32, (3) the amino acid sequence of SEQ ID NO: 34, or an amino acid sequence having a substitution, insertion, or deletion of one or several amino acids at a moiety except for CDR1 (SEQ ID NO: 16), CDR2 (RAN), and CDR3 (SEQ ID NO: 18) in the amino acid sequence of SEQ ID NO: 34, and (4) the amino acid sequence of SEQ ID NO: 36, or an amino acid sequence having a substitution, insertion, or deletion of one or several amino acids at a moiety except for CDR1 (SEQ ID NO: 22), CDR2 (RAN), and CDR3 (SEQ ID NO: 24) in the amino acid sequence of SEQ ID NO: 36.

6. The antibody or the antibody derivative according to claim 1, wherein the antibody or the antibody derivative is selected from the group consisting of:

(1-1) an antibody or an antibody derivative comprising the amino acid sequence of SEQ ID NO: 37, or an amino acid sequence having a substitution, insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 37 and the amino acid sequence of SEQ ID NO: 38, or an amino acid sequence having the substitution, insertion, or deletion of one or several amino acids at a moiety except for CDR1 (SEQ ID NO: 4), CDR2 (GAT), and CDR3 (SEQ ID NO: 6) in the amino acid sequence of SEQ ID NO: 38;

(1-2) the amino acid sequence of SEQ ID NO: 39, or an amino acid sequence having the substitution, insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 39 and the amino acid sequence of SEQ ID NO: 40, or an amino acid sequence having the substitution, insertion, or deletion of one or several amino acids at a moiety except for CDR1 (SEQ ID NO: 4), CDR2 (GAT), and CDR3 (SEQ ID NO: 6) in the amino acid sequence of SEQ ID NO: 40);

(1-3) the amino acid sequence of SEQ ID NO: 41, or an amino acid sequence having the substitution, insertion, or deletion of one or several amino acids at a moiety except for CDR1 (SEQ ID NO: 1), CDR2 (SEQ ID NO: 2), and CDR3 (SEQ ID NO: 3) in the amino acid sequence of SEQ ID NO: 41 and the amino acid sequence of SEQ ID NO: 42, or an amino acid sequence having the substitution, insertion, or deletion of one or several amino acids at a moiety except for CDR1 (SEQ ID NO: 4), CDR2 (GAT), and CDR3 (SEQ ID NO: 6) in the amino acid sequence of SEQ ID NO: 42;

(2) an antibody or an antibody derivative comprising the amino acid sequence of SEQ ID NO: 43, or an amino acid sequence having the substitution, insertion, or deletion of one or several amino acids at a moiety except for CDR1 (SEQ ID NO: 7), CDR2 (SEQ ID NO: 8), and CDR3 (SEQ ID NO: 9) in the amino acid sequence of SEQ ID NO: 43 and the amino acid sequence of SEQ ID NO: 44, or an amino acid sequence having the substitution, insertion, or deletion of one or several amino acids at a moiety except for CDR1 (SEQ ID NO: 10), CDR2 (SEQ ID NO: 11 RAN), and CDR3 (SEQ ID NO: 12) in the amino acid sequence of SEQ ID NO: 44;

(3) an antibody or an antibody derivative comprising the amino acid sequence of SEQ ID NO: 45, or an amino acid sequence having the substitution, insertion, or deletion of one or several amino acids at a moiety except for CDR1 (SEQ ID NO: 13), CDR2 (SEQ ID NO: 14), and CDR3 (SEQ ID NO: 15) in the amino acid sequence of SEQ ID NO: 45 and the amino acid sequence of SEQ ID NO: 46, or an amino acid sequence having the substitution, insertion, or deletion of one or several amino acids at a moiety except for CDR1 (SEQ ID NO: 16), CDR2 (RAN), and CDR3 (SEQ ID NO: 18) in the amino acid sequence of SEQ ID NO: 46; and (4) the amino acid sequence of SEQ ID NO: 47, or an amino acid sequence having the substitution, insertion, or deletion of one or several amino acids at a moiety except for CDR1 (SEQ ID NO: 19), CDR2 (SEQ ID NO: 20), and CDR3 (SEQ ID NO: 21) in the amino acid sequence of SEQ ID NO: 47 and the amino acid sequence of SEQ ID NO: 48, or an amino acid sequence having the substitution, insertion, or deletion of one or several amino acids at a moiety except for CDR1 (SEQ ID NO: 22), CDR2 (RAN), and CDR3 (SEQ ID NO: 24) in the amino acid sequence of SEQ ID NO: 48.

7. A pharmaceutical composition for treating bleeding caused by the excessive cleavage of VWF, comprising the antibody or the antibody derivative according to any claim 1.

8. The pharmaceutical composition according to claim 7, wherein the bleeding caused by the excessive cleavage of VWF is bleeding associated with mechanical assisted circulation.

9. The pharmaceutical composition according to claim 7, wherein the pharmaceutical composition inhibits the cleaving activity of ADAMTS13 against VWF.

10. The pharmaceutical composition according to claim 7, wherein the bleeding associated with mechanical assisted circulation is acquired von Willebrand syndrome (AVWS).

11. The pharmaceutical composition according to claim 7, wherein the mechanical assisted circulation is selected from the group consisting of extracorporeal membrane oxygenation (ECMO), implantable left ventricular assist device (LVAD), and percutaneous cardiopulmonary support (PCPS).

12. A method for detecting and/or measuring the presence or an amount of ADAMTS13 in a biological sample, comprising:

contacting the biological sample collected from a test subject with the antibody or the antibody derivative according to claim 1 in vitro; and detecting and/or measuring ADAMTS13 in the sample bound with the antibody or the antibody derivative.

13. A kit for detecting and/or measuring the presence or an amount of ADAMTS13 in the body of a test subject, comprising the antibody or the antibody derivative according to claim 1.

14. A method for detecting and/or measuring the VWF cleaving activity of ADAMTS13 in a biological sample, comprising:

adding varying concentrations of the antibody or the antibody derivative according to claim 1 to the biological sample collected from a test subject, followed by incubation; and detecting and/or measuring an intact VWF multimer, an intact VWF monomer, or a cleaved VWF fragment in the sample.

15. A kit for detecting and/or measuring an intact VWF multimer, an intact VWF monomer, or a cleaved VWF fragment in the body of a test subject, comprising the antibody or the antibody derivative according to claim 1.

* * * * *